United States Patent [19]
Mulier et al.

[11] Patent Number: 5,807,395
[45] Date of Patent: Sep. 15, 1998

[54] METHOD AND APPARATUS FOR RF ABLATION AND HYPERTHERMIA

[75] Inventors: Peter M. J. Mulier, St. Paul; Michael F. Hoey, Shoreview, both of Minn.

[73] Assignee: Medtronic, Inc.

[21] Appl. No.: 837,737

[22] Filed: Apr. 22, 1997

Related U.S. Application Data

[63] Continuation of Ser. No. 394,691, Feb. 22, 1995, abandoned, which is a continuation-in-part of Ser. No. 113,441, Aug. 27, 1993, Pat. No. 5,431,649.

[51] Int. Cl.$^6$ .................................................. A61B 17/39
[52] U.S. Cl. ............................... 606/41; 606/41; 604/22; 607/101; 607/102
[58] Field of Search .................................. 606/27–34, 41, 606/42, 45–50; 607/100–105, 154, 156; 604/21, 22; 600/372–374

[56] References Cited

U.S. PATENT DOCUMENTS

| | | |
|---|---|---|
| 4,307,720 | 12/1981 | Weber, Jr. . |
| 4,506,680 | 3/1985 | Stokes . |
| 4,641,649 | 2/1987 | Walinsky et al. . |

(List continued on next page.)

FOREIGN PATENT DOCUMENTS

| | | |
|---|---|---|
| 0370890 | 5/1990 | European Pat. Off. . |
| 0499491 | 8/1992 | European Pat. Off. . |
| 0500215 | 8/1992 | European Pat. Off. . |
| 0500289 | 8/1992 | European Pat. Off. . |
| 9006079 | 6/1990 | WIPO . |
| 9410924 | 5/1994 | WIPO . |
| 9410925 | 5/1994 | WIPO . |
| 9411059 | 5/1994 | WIPO . |

OTHER PUBLICATIONS

"Differential Response of Normal and Tumor Microcirculation to Hyperthermia," by T. E. Dudar et al, *Cancer Research*, vol. 44, Feb. 1984, pp. 605–612.

"Progress in Hyperthermia?," by J. R. Oleson, *Int. J. Radiation Oncology, Biology, Physics*, vol. 20, (Feb. 1991), pp. 1143–1144.

"Percutaneous Transperineal Prostate Cryosurgery Using Transrectal Ultrasound Guidance: Animal Model," by G. Onik et al., *Urology*, vol. 37, No. 3, (Mar. 1991) p. 277.

(List continued on next page.)

*Primary Examiner*—Michael Peffley
*Attorney, Agent, or Firm*—Harold R. Patton; Peter Forrest

[57] ABSTRACT

A methods and apparatuses for ablation or hyperthermic treatment of body tissue are disclosed, wherein the application of radio-frequency ablative or hyperthermic energy is accompanied by the infusion of a conductive solution into the tissue, such that a virtual electrode is created. The virtual electrode results from the increased conductivity of the tissue in the area being treated due to the presence of conductive solution, such that the area of tissue being treated is enlarged as compared with non-fluid-assisted application of energy. In one embodiment, a catheter having a hollow helical electrode/needle on the distal end thereof is provided, such that the electrode/needle can be screwed into the tissue to be treated. A conductive fluid, such as saline, saturated saline, or Ringer's solution, is infused into the tissue to be treated via the hollow electrode and a lumen extending along the length of the catheter. In another embodiment of the invention, an implantable infusion port for fluid-assisted ablation and/or hyperthermia is provided with an elongate catheter having a hollow electrode/needle on the distal end thereof. The port is subcutaneously implanted with the electrode/needle situated within the tissue to be treated. A percutaneous needle facilitates the introduction of conductive fluid and/or chemotherapeutic agents into the tissue via a lumen in the catheter and the hollow electrode/needle. The percutaneous needle also makes electrical contact with a conductor in the catheter, such that as fluid is being introduced into the tissue, radio-frequency energy may be applied to the tissue being treated.

10 Claims, 23 Drawing Sheets

U.S. PATENT DOCUMENTS

| | | |
|---|---|---|
| 4,674,498 | 6/1987 | Stasz . |
| 4,682,596 | 7/1987 | Bales et al. . |
| 4,748,979 | 6/1988 | Hershenson . |
| 4,802,476 | 2/1989 | Norenberg et al. . |
| 4,832,048 | 5/1989 | Cohen . |
| 4,850,353 | 7/1989 | Stasz et al. . |
| 4,862,890 | 9/1989 | Stasz et al. . |
| 4,869,248 | 9/1989 | Narula . |
| 4,896,671 | 1/1990 | Cunningham et al. . |
| 4,936,281 | 6/1990 | Stasz . |
| 4,966,597 | 10/1990 | Cosman . |
| 4,976,711 | 12/1990 | Parins et al. . |
| 4,977,902 | 12/1990 | Sekino et al. . |
| 4,979,948 | 12/1990 | Geddes et al. . |
| 5,056,517 | 10/1991 | Fenici . |
| 5,057,107 | 10/1991 | Parins et al. . |
| 5,078,717 | 1/1992 | Parins et al. . |
| 5,083,565 | 1/1992 | Parins . |
| 5,087,256 | 2/1992 | Taylor et al. . |
| 5,098,431 | 3/1992 | Rydell . |
| 5,122,137 | 6/1992 | Lennox . |
| 5,125,928 | 6/1992 | Parins et al. . |
| 5,129,396 | 7/1992 | Rosen et al. . |
| 5,150,717 | 9/1992 | Rosen et al. . |
| 5,171,311 | 12/1992 | Rydell et al. . |
| 5,178,618 | 1/1993 | Kandarpa . |
| 5,188,635 | 2/1993 | RadtKe . |
| 5,192,280 | 3/1993 | Parins . |
| 5,197,963 | 3/1993 | Parins . |
| 5,197,964 | 3/1993 | Parins . |
| 5,215,103 | 6/1993 | Desai . |
| 5,220,927 | 6/1993 | Astrahan et al. . |
| 5,234,004 | 8/1993 | Hascoet et al. . |
| 5,242,442 | 9/1993 | Hirschfeld . |
| 5,269,781 | 12/1993 | Howell, III . |
| 5,277,201 | 1/1994 | Stern . |
| 5,281,217 | 1/1994 | Edwards et al. . |
| 5,281,218 | 1/1994 | Imran . |
| 5,290,286 | 3/1994 | Parins . |
| 5,336,222 | 8/1994 | Durgin, Jr. et al. ........................ 606/50 |
| 5,342,357 | 8/1994 | Nardella ..................................... 606/40 |
| 5,348,554 | 9/1994 | Imran et al. ............................... 606/41 |
| 5,370,675 | 12/1994 | Edwards et al. . |
| 5,385,544 | 1/1995 | Edwards et al. ......................... 607/101 |
| 5,403,311 | 4/1995 | Abele et al. ............................... 606/49 |
| 5,413,588 | 5/1995 | Rudi e et al. . |
| 5,415,654 | 5/1995 | Daikuzono . |
| 5,431,649 | 7/1995 | Mulier et al. ............................ 128/642 |
| 5,454,807 | 10/1995 | Lennox et al. . |
| 5,458,597 | 10/1995 | Edwards et al. ........................... 606/41 |
| 5,464,437 | 11/1995 | Rei d et al. . |
| 5,496,271 | 3/1996 | Burton et al. . |
| 5,505,730 | 4/1996 | Edwards ..................................... 606/41 |
| 5,507,743 | 4/1996 | Edwards et al. ........................... 606/48 |
| 5,599,294 | 2/1997 | Edwards et al. . |

OTHER PUBLICATIONS

"Physical and Dynamic Characteristics of DC Ablation in Relation to the Type of Energy Delivery and Catheter Design," by Robert Lemery et al., *PACE,* vol. 14, Jul. 1991, pp. 1158–1198.

"Basic and Clinical Studies of Local Hypothermia For Prostatic Cancer," by Masataka Hirai, *Nippon Hinyokika Gakkai Zasshi,* vol. 83, No. 5, May 1992, pp. 597–604.

"Interstitial Laser Hyperthermia," by A. Masters et al., *Seminars in Surgical Oncology,* vol. 8, (1992), pp. 242–249.

"Prediction of Treatment Temperatures in Clinical Hyperthermia of Locally Advanced Breast Carcinoma: The Use of Contrast Enhanced Computer Tomography," by H. Lyng et al., *Int. J. Radiation Oncology, Biol. Phys.,* vol. 26, (Jan. 1993), pp. 451–457.

"Thermometry of Interstitial Hyperthermia Given as an Adjuvant to Brachytherapy for the Treatment of Carcinoma of the Prostate," by S. D. Prionas et al., *Int. J. Radiation Oncology, Biol. Phys.,* vol. 28. (Sep. 1993), pp. 151–162.

"Transurethral Radio Frequency Thermomtherapy for Symptomatic Benign Proststic Hyperplasia," by A. Corica et al., *Eur Urol,* vol. 23, 1993, pp. 312–317.

"Benign Prostatic Hypertrophy Treatment by Transurethral Radiofrequency Hyperthermia with Thermex II," by J.L. Viguier et al., *Eur Urol,* vol. 23, 1993, pp. 318–321.

"Transurethral Thermotherapy of the Benign Prostate Hypertrophy Controlled by Radiometry," by G. Belot et al., *Eur Urol,* vol. 23, 1993, pp. 326–329.

"Transurethral Needle Ablation (TUNA) of the Prostate Using Low–Level Radiofrequency Energy: An Animal Experimental Study," by B. Goldwasser et al., *Eur Urol,* vol. 24, 1993, pp. 400–405.

"Needle Ablation Using Radio Frequency Current as a Treatment of Benign Prostatic Hyperplasia: Experimental Results in ex vivo Human Prostate," by J. Ramon et al., *Eur Urol,* vol. 24, 1993, pp. 406–410.

"Transurethral Needle Ablation (TUNA): Thermal Gradient Mapping and Comparison of Lesion Size in a Tissue Model and in Patients with Benign Prostatic Hyperplasia," by J.S. Rasor et al., *Eur Urol,* vol. 24, 1993, pp. 411–414.

"Transurethral Needle Ablation (TUNA): Safety, Feasibility, and Tolerance of a New Office Procedure for Treatment of Benign Prostatic Hyperplasia," by C.C. Schulman et al., *Eur Urol,* vol. 24, 1993, pp. 415–423.

"Cooled Tip Ablation Results in Increased Radiofrequency Power Delivery and Lesion Size," *PACE,* vol. 17, Apr. 1994, Part II, p. 782.

"Barriers to Drug Delivery in Solid Tumors," by R. K. Jain, *Scientific American,* vol. 271, No. 1, (Jul. 1994), pp. 58–65.

"Hyperthermia in Cancer Therapy: Where Are We Today and Where Are We Going?" by R. A. Steeves, *Bull. NY Acad. Med. (U.S.)* vol. 68, No. 2, Mar.–Apr., pp. 341–350.

Abstract 832 "Hydro–Ablation: A New Method for Trans–Catheter Radiofrequency Ablation," by S.W. Adler, et al., *EUR.J.C.P.E.,* vol. 4, No. 2, Jun. 1994.

Abstract 165, "Comparison of Radiofrequency (RF) Versus Microwave (MW) Energy Catheter Ablation of the Bovine Ventricular Mycardium," by L..A. Pires, M.D. et al., *PACE,* vol. 17, Apr. 1994, Part II.

Abstract 166, "Developing and Testing a Feedback Control System for Microwave Ablation: In Vitro and In Vivo Results," by P.J. Wang, M.D. et al, *PACE,* vol. 17, Apr. 1994, Part II.

Abstract 168, "Laser and Radiofrequency Catheter Ablation of Ventricular Myocardium in Dogs: a Comparative Test," by S. Enders, M.D. et al, *PACE,* vol. 17, Apr. 1994, Part II.

Abstract 0872, "Radiofrequency Delivery Through an Endocardial Cooled Catheter Results in Increased Lesion Size," by R. Ruffy et al, University of Utah, Salt Lake City, UT.

Abstract 0873, "Porous Metal Tipped Catheter Produces Larger Radiofrequency Lesions Through Tip Cooling," by D. Bergau et al, Children's Hospital, Boston, MA.

Abstract 287, "Comparison of Transesophageal Echocardiographic Guidance of Transseptal Left Heart Catheterization During Mitral Valvuloplasty and Radiofrequency Ablation of Left–Sided Accessory Pathways," by K.J. Tucker. M.D. et al, *PACE,* vol. 17, Apr. 1994, Part II.

Abstract 288, "Microwave Catheter Ablation via the Coronary Sinus: The Need for Power and Temperature Regulation?," by P.J. Wang, M.D. et al, *PACE,* vol. 17, Apr. 1994, Part II.

Abstract 290, "Electrode Temperature During Radiofrequency Catheter Ablation Procedures: Relationship to Ablation Target and Ablation Result," by H. Calkins, M.D. et al, *PACE,* vol. 17, Apr. 1994, Part II.

Abstract 485, "Comparison of Tissue Temperature and Lesion Size in Radiofrequency Ablation Using Saline Irrigation with a Small Versus Large Tip Electrode in a Canine Thigh Muscle Preparation," by H. Nakagawa, M.D. et al, *PACE,* vol. 17, Apr. 1994, Part II.

Abstract 487, "Intramural Ablation Using Radiofrequency Energy Via Screw–Tip Catheter and Saline Electrode," by M.F. Hoey MS, et al, *PACE,* vol. 17, Apr. 1994, Part II.

Abstract 1291, "Increase in the Lesion Size and Decrease in the Impedance Rise with a Saline Infusion Electrode Catheter for Radiofrequency Catheter Ablation," by S.K. Stephen Huang et al., *Circulation,* vol. 80, No. 4, Oct. 1989.

Abstract 121, "Tissue Temperature in Radiofrequency Ablation Using a Saline Irrigated Electrode Versus Temperature Monitoring in a Canine Thigh Muscle Preparation," by H. Nakagawa et al., *Abstracts from the 67th Scientific Sessions.*

"Use of Saline Infusion Electrode Catheter for Improved Energy Delivery and Increased Lesion Size in Radiofrequency Catheter Ablation," by R.S. Mittleman et al., *PACE,* May 1995, Part I.

Abstract 705–5, "Comparison of Radiofrequency Lesions in the Canine Left Ventricle Using a Saline Irrigated Electrode Versus Temperature Control," by H. Nakagawa et al., *JACC,* Feb. 1995, p. 42A.

Abstract 777–1, "Effective Delivery of Radiofrequency Energy Through the Coronary Sinus without Impedance Rise Using a Saline Irrigated Electrode," by H, Nakagawa et al., *JACC,* Feb. 1995, p. 293A.

Abstract 22, "Tip Temperature is not an Indicator of Intramyocardial Temperatures During Radiofrequency Catheter Ablation," by Sean Mackey, MD, et al, *PACE,* vol. 17, Apr. 1994, Part II.

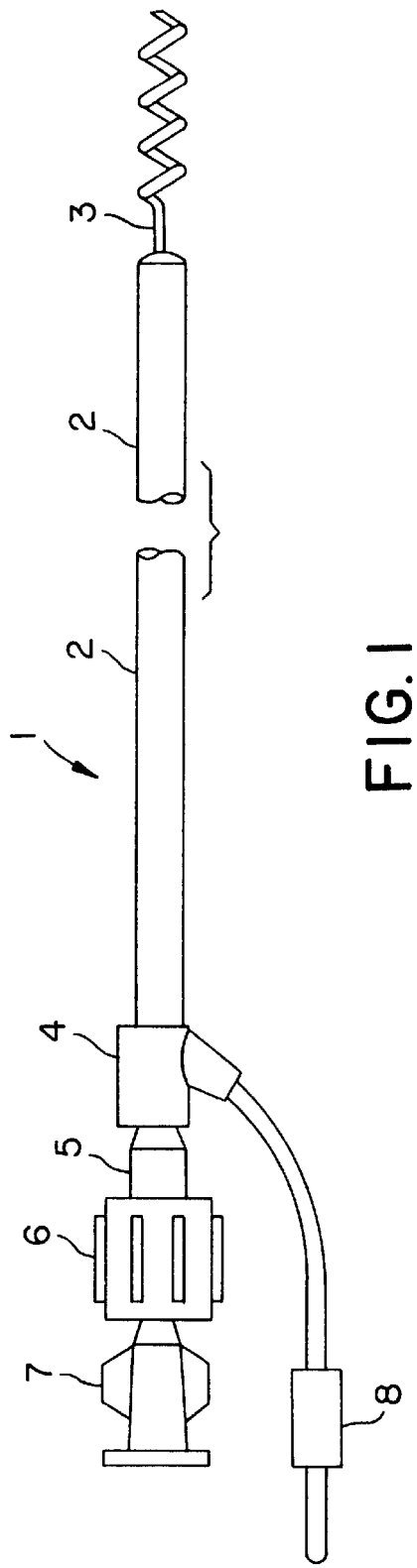
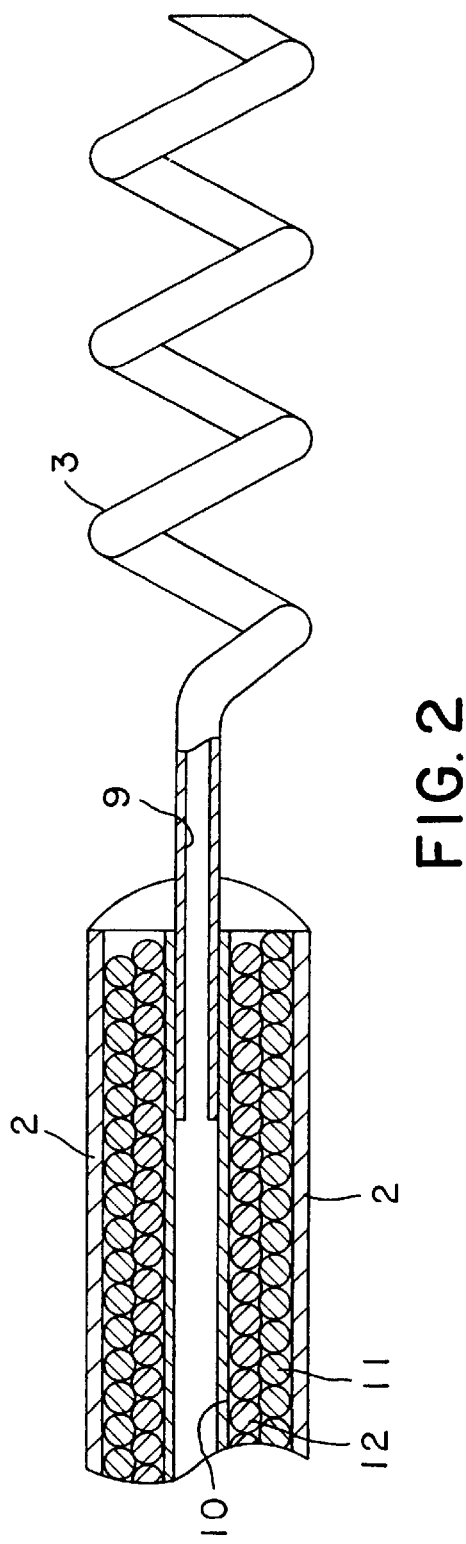
FIG. 1
FIG. 2

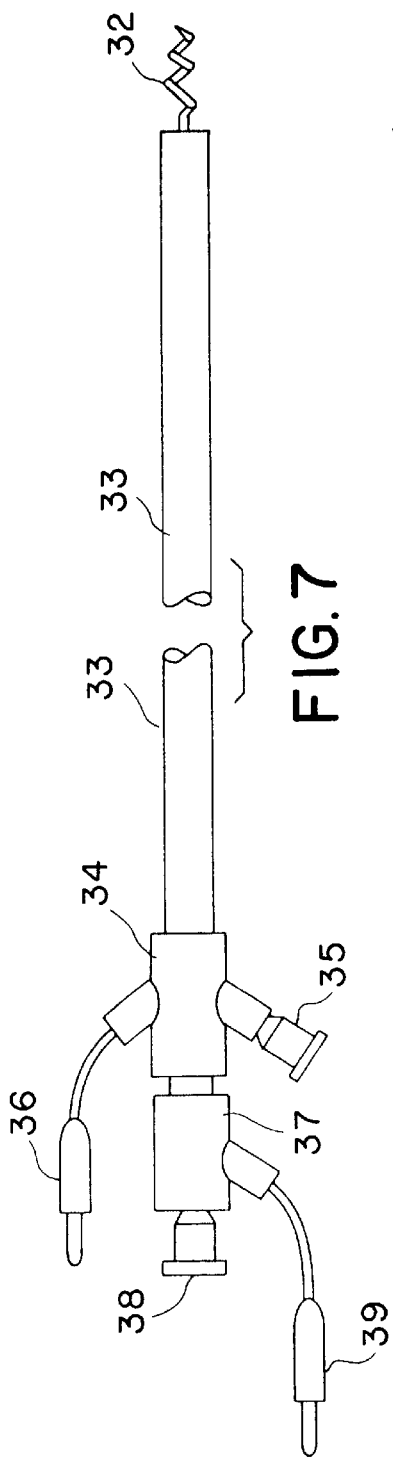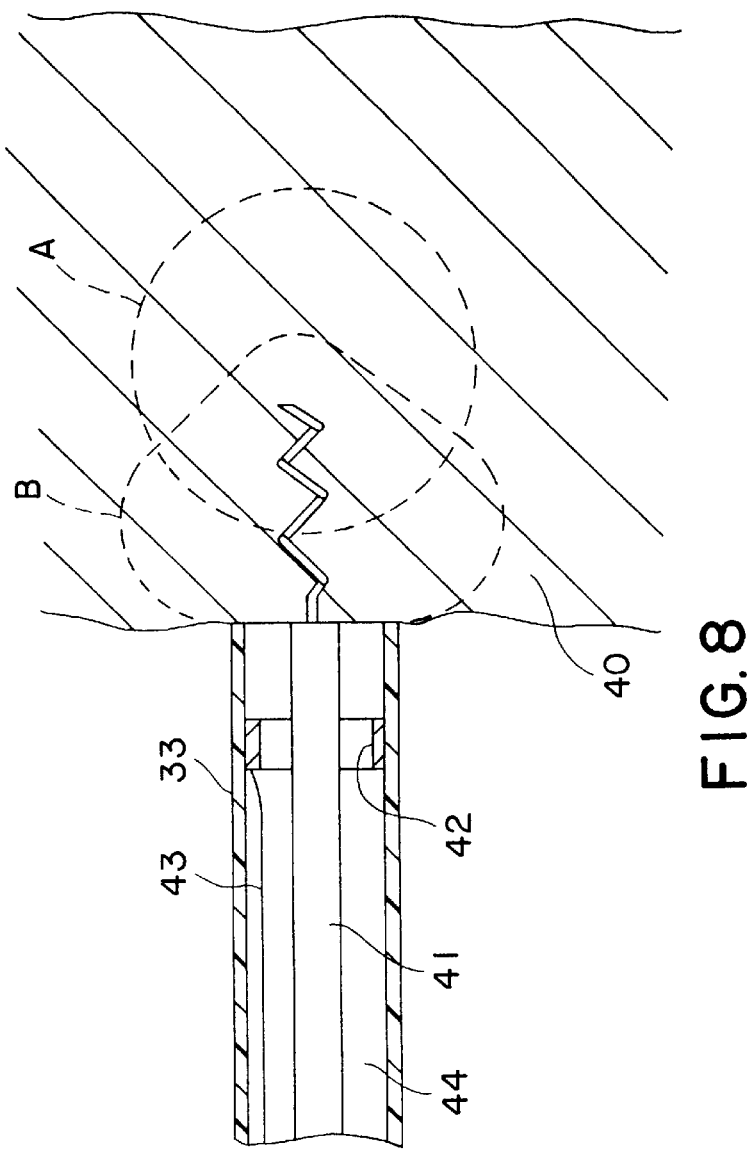

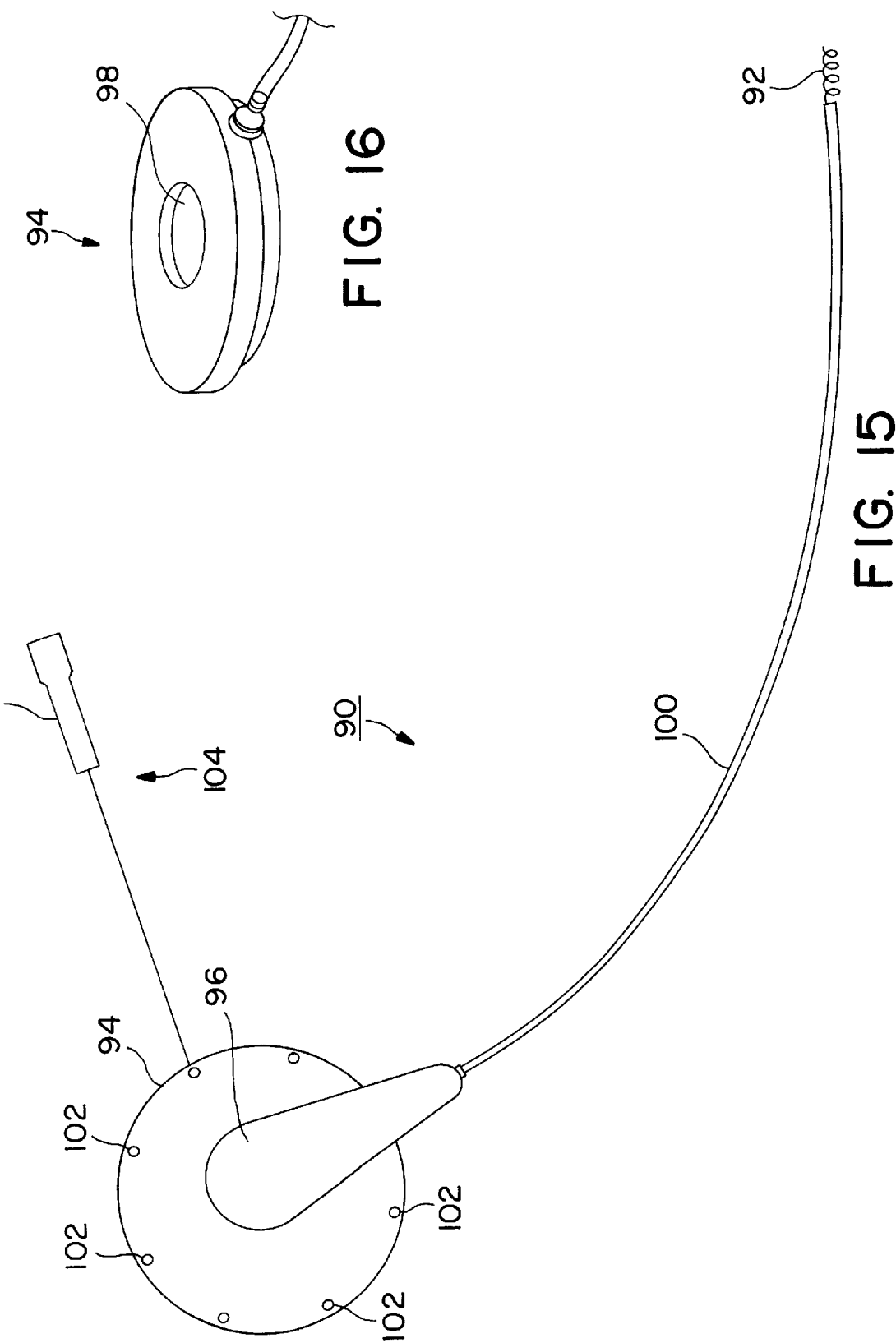

METHOD AND APPARATUS FOR RF ABLATION AND HYPERTHERMIA

RELATED APPLICATIONS

This application is a continuation of application Ser. No. 08/394,691, filed Feb. 22, 1995, now abandoned, which is a continuation-in-part of application Ser. No. 08/113,441, filed Aug. 27, 1993 now U.S. Pat. No. 5,431,649.

FIELD OF THE INVENTION

This invention relates generally to the field of medical procedures, and more particularly relates to a method and apparatus for ablating body tissue.

BACKGROUND OF THE INVENTION

The above-referenced '441 application is primarily directed toward ablative treatment of tachyarrhythmias, which are heart rhythms in which a chamber of the heart exhibits an excessively fast rhythm. The '441 application is in particular directed toward treatment of tachyarrhythmias resulting from the presence of ectopic foci within the cardiac tissue or from the presence of aberrant conduction pathways within the cardiac tissue.

As noted in the '441 application, therapies have been developed for treating tachycardias by destroying cardiac tissue containing identified ectopic foci or aberrant conduction pathways. A variety of approaches have been taken, including application of electrical energy or other forms of energy to destroy the undesired cardiac tissue. As examples, ablation of cardiac tissue has been accomplished by means of radio frequency (RF) electrical current, microwave energy, heat, electrical pulses, cryotherapy, and lasers. At present, ablation using RF energy is perhaps the most widely practiced in the context of ablation procedures that can be carried out by means of a catheter, inserted transvenously into the closed heart.

Most RF ablation catheters for ablation of cardiac tissue employ electrodes which are intended to contact the endocardium of the heart, or, in some cases, as in U.S. Pat. No. 5,083,565, are intended to penetrate the endocardium, and enter the myocardium. In general, RF ablation catheters are effective to induce small lesions in heart tissue including the endocardium and inner layers of myocardium, in the immediate vicinity of the electrode. However, the medical community has expressed a desire for devices which produce larger lesions, to reduce the number of applications of RF energy (burns) required to effectively ablate the cardiac tissue associated with the tachycardia.

RF ablation causes tissue in contact with the electrode to heat through resistance of the tissue to the induced electrical current therethrough. The actual extent of heating is somewhat unpredictable. However, temperature tends to rise as the duration and amplitude of the RF signal increases. Heating of the tissue beyond a certain point can undesirably cause desiccation or charring of the tissue, resulting in a high impedance between the RF electrode and the return electrode, in turn leading to cessation of the heating process, and, in some cases, sticking of the electrode to the charred tissue. Localized heating of tissue near an ablation electrode is not only a function of the amplitude of ablative RF energy applied, but is also a function of time, electrode size, and tissue conductivity, among other factors. Depending upon the combination of such factors, for a given ablative energy level the tissue may not have sufficient time to conduct the resultant heat away from the electrode, leading to desiccation and burning of tissue near the electrode. The burned tissue then creates a barrier that effectively prevents the transmission of RF energy to more distant tissue.

One response to this phenomenon has been the inclusion of thermocouple within the ablation electrode, in conjunction with feedback control to modulate the RF signal to maintain the electrode temperature at a set parameter. One such system is disclosed in U.S. Pat. No. 5,122,137; this approach is also proposed in U.S. Pat. No. 5,348,554 to Imran et al., entitled "Catheter for RF Ablation With Cooled Electrode."

The Imran et al. '554 patent also proposes circulating chilled fluid through a cavity disposed behind the distal electrode of an ablation catheter, in order to minimize heating of the electrode during ablation procedures. To this end, the Imran et al. '554 patent proposes communicating chilled fluid (e.g., saline) from the proximal end of the electrode to the cavity behind the electrode via a first (supply) lumen extending along the length of the catheter. In one embodiment, the chilled fluid is returned to the proximal end of the catheter via a second (return) lumen, while in an alternative embodiment, the chilled fluid is allowed to exit the cavity via holes provided in the electrode. The Imran et al. '554 patent describes such introduction of saline into the blood as "not objectionable."

Other references which appear to address the problem of undesirable heating at an ablation site include: Sykes et al., "Cooled Tip Ablation Results in Decreased Radiofrequency Power Delivery and Lesion Size," PACE, Vol. 17, April 1994, Part II, p. 782; U.S. Pat. No. 5,334,193 to Nardella, entitled "Fluid Cooled Ablation Catheter;" PCT patent application no. PCT/US93/10465, filed in the name of Nardella and entitled "Fluid Cooled Ablation Catheter;" PCT patent application no. PCT/US93/10466, filed in the name of Nardella and entitled "Fluid Cooled Electrosurgical Probe;" and PCT patent application no. PCT/US93/10467, filed in the name of Nardella and entitled "Fluid Cooled Electrosurgical Cauterization System."

The '441 application proposes improving the consistency and efficacy of RF ablation by increasing the overall size and extent of the lesions induced by RF ablation. In particular, the '441 application proposes an ablation catheter which includes a helical electrode intended to be screwed into the myocardium at the site intended for ablation. The helical electrode provides an enlarged surface area as compared to relatively straight or needle-like electrodes for insertion into the endocardium, and also serves to stabilize the location of the catheter during the application of the RF signal. In addition, there is essentially no bleeding following removal of the helical electrode, so it can safely be placed in multiple locations for mapping and ablation purposes.

An additional aspect of the invention disclosed in the '441 application in its preferred embodiment is the provision of a non-toxic, non-arrhythmogenic, conductive solution such as Ringer's solution to the area of the electrode, before and during application of RF energy. In that embodiment, the helical electrode is hollow, and the conductive solution is applied through one or more apertures in the electrode. The conductive solution injected prior to application of the RF signal is believed to displace blood in the vicinity of the electrode. Ringer's solution, for example, has a much higher conductivity than blood (approximately three to four times) or cardiac muscle (approximately seven times); thus, overall resistance to the induced electrical current is reduced, which is believed to assist in expanding the size of the lesion by spreading the effective area of application of the electrical current over a wider area. Application of the conductive solution during the ablation process further assists by preventing overheating of the tissue, allowing for a prolonged application of the RF signal, extending beyond the point at which burning or charring would otherwise normally occur. Both of these factors are believed to contribute to an increase in the overall size of the lesion produced by application of RF energy at a particular location.

An alternative embodiment of the helical needle ablation catheter described in the '441 application is proposed in co-pending U.S. patent application Ser. No. 08/303,246, entitled "Method and Apparatus for RF Ablation," filed on Sep. 8, 1994 in the name of Peter M. J. Mulier. The '246 application is commonly assigned to the assignee of the present invention and is hereby incorporated by reference herein in its entirety.

According to the '246 disclosure, the helical needle ablation catheter may be further provided with a second electrode, recessed within a lumen open to the distal end of the catheter body. The open end of the lumen is held against heart tissue by the helical electrode, and the lumen is filled with a conductive fluid which serves to electrically couple the recessed electrode to the tissue. The two electrodes (i.e., the helical needle and the recessed electrode) may be used alone or in conjunction with one another, to produce lesions of varying shape and location.

Further in accordance with the '246 disclosure, the catheter may be adapted to deliver a chilled fluid, such as Ringer's solution, through the helical electrode into the tissue adjacent to the electrode. The chilled fluid may be used to cool the tissue in a fashion similar to cryo-mapping. Directional injection of the chilled fluid allows for testing of multiple adjacent tissue locations by simply rotating the helical electrode, without having to reposition the catheter. The '246 disclosure further suggests that subsequent directional delivery of fluid may also be employed in conjunction with ablation of tissue.

The delivery of conductive fluid to tissue undergoing RF ablation is also proposed in co-pending U.S. patent application Ser. No. 08/302,304 entitled "Method and Apparatus for RF Ablation," filed on Sep. 8, 1994 in the name of Peter M. J. Mulier and Michael F. Hoey. The '304 application is commonly assigned to the assignee of the present invention and is hereby incorporated by reference herein in its entirety. In one embodiment disclosed in the '304 application, the electrode takes the form of an elongated conductive coil mounted around a distal portion of the catheter body, which itself is porous to allow flow of fluid out of the catheter in the vicinity of the electrode coil.

While the ablation methods and apparatuses proposed in the above-referenced '441, '246, and '304 applications are believed to offer advantages over the prior art, it is believed that there nonetheless remains room for improvements in the field of ablation, particularly with regard to the consistency and efficacy thereof, and also with regard to the applicability of fluid-assisted ablation techniques to ablation of tissue other than cardiac tissue. Moreover, it is believed that the fluid-assisted techniques may also be advantageously applied in the context of hyperthermic treatments.

SUMMARY OF THE INVENTION

In view of the foregoing considerations, the present invention is directed to a method and apparatus for ablation or hyperthermia of body tissue.

In accordance with one aspect of the invention, a catheter for performing "fluid assisted" ablation or hyperthermia is provided with the capability of infusing a conductive solution, e.g., saline, saturated saline, Ringer's, or the like, into tissue prior to and during application of ablative or hyperthermic RF energy. In one embodiment, this is accomplished by means of a hollow needle which serves both as an electrode and as a conduit for the infused fluid.

In accordance with the present invention, the infusion of conducting fluid into the area of ablation or hyperthermia prior to and during the application of RF energy creates what is referred to herein as a "virtual electrode," the size and shape of which can be controllably modified, and which can be rendered more or less conductive, thereby modifying the spread of RF energy. The rate of infusion and conductivity of the perfusate can be controlled to work in conjunction with various electrodes with different surface areas. Different body tissues or tumors may require different sizes and shapes of electrodes for access and penetration. A smaller surface area metal contact electrode typically necessitates the use of a more conductive solution to effectively spread the energy and prevent desiccation at the electrode-tissue interface. By varying such factors as the RF energy and duration, the extent of pre-RF infusion, the RF infusion rate and conductivity of solution, the electrode size, shape, and surface area, the size, shape, and intensity of the "virtual electrode"—i.e., the intensity of thermal production in the ablation or hyperthermia area, can be controlled.

In one embodiment of the invention, a hollow, helical ("screw-in") needle is disposed on the distal end of an ablation catheter adapted to be used in ablation tissue in various organs, tissues, and tumors in the body that would benefit from ablation to inhibit growth, debulk, or simply cease function of a pathological state. Tissue or tumor sites for which the present invention is believed to be applicable include, without limitation: prostate, breast, brain, neck, lung, lymphoid regions, esophagus, gastric mass, pancreas, liver, small intestines, large intestines, colon, ovaries, testis, pelvic region, uterus, cervix, oral cavity, larynx, bladder, kidney, and muscle.

In accordance with one embodiment of the invention, a long-term implantable infusion and ablation or hyperthermia port is provided for facilitating repeated treatment of a site within the body using fluid-assisted techniques. The infusion port includes a subcutaneously implantable main body for enabling percutaneous communication of both infusion fluid and RF energy. A lead extending from the main body terminates at its distal end with a hollow, helical needle adapted to be screwed in to the desired site for ablation or hyperthermia.

BRIEF DESCRIPTION OF THE DRAWINGS

The foregoing and other aspects of the present invention in its various embodiments may perhaps be best appreciated with reference to detailed descriptions of specific embodiments of the invention, when read in conjunction with the accompanying drawings, wherein:

FIG. 1 is a plan view of a catheter adapted to perform RF ablation or hyperthermia in accordance with the present invention;

FIG. 2 is a cutaway view through the distal end of the catheter illustrated in FIG. 1;

FIG. 7 illustrates an alternative embodiment to the catheter of FIGS. 1 and 2, employing a second, recessed electrode;

FIG. 8 illustrates a cut-away view of the catheter of FIG. 7, with its helical electrode located in heart tissue;

FIG. 15 is a top view of an infusion and ablation/hyperthermia port in accordance with one embodiment of the present invention;

FIG. 16 is a perspective view of the body portion of the infusion and ablation/hyperthermia port from FIG. 15;

DETAILED DESCRIPTION OF SPECIFIC EMBODIMENTS OF THE INVENTION

Figure 3:
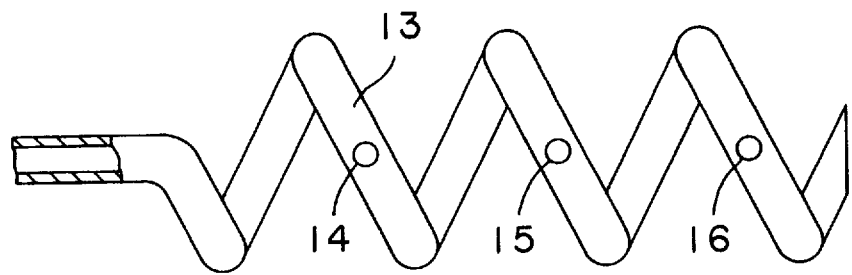
FIGS. 3, 4, and 5 illustrate alternative embodiments of the helical electrode of the catheter illustrated in FIGS. 1 and 2.

FIG. 1 is a plan view of a catheter designed for performing RF ablation or hyperthermia in accordance with the present invention. The catheter of FIG. 1 includes an elongated catheter body 1, comprising an insulative outer sheath 2, which may be made of polyurethane, Teflon, or other biocompatible plastic. A hollow, helical electrode 3 is located at the distal end of the catheter and is coupled to the distal end of an internal tube, running the length of the catheter. At the proximal end of the catheter a fitting 4 is located, to which Luer lock 5 is coupled. Luer lock 5 is coupled to the proximal end of the internal tube. A swivel mount 6 is mounted to Luer lock 5, allowing rotation of the catheter relative to Luer lock 7. Luer lock 7 is intended to be coupled to a source of conductive fluid such as Ringer's solution, and allows for application of the Ringer's solution through the catheter and through electrode 3, while electrode 3 is being screwed into heart tissue. An electrical connector 8 exits fitting 4, and is coupled to electrode 3, allowing for the use of electrode 3 to apply RF energy to body tissue. As noted in the above-referenced '441 application, if the catheter of FIG. 1 is being used to perform cardiac ablation, electrode 3 may also be employed for other related functions such as measurement of electrical cardiac signals, and pacing of heart tissue by application of low energy pulses appropriate for cardiac pacing.

In use for cardiac ablation, the catheter is advanced to the desired site, which preferably has been previously identified by means of cardiac mapping in a fashion similar to cardiac mapping presently employed with RF ablation procedures. The catheter may be guided to the desired location by being passed down a steerable or guidable catheter, for example, as disclosed in U.S. Pat. No. 5,030,204, issued to Badger et al., or by means of a fixed configuration guide catheter, for example in U.S. Pat. No. 5,104,393, issued to Isner, both of which patents are incorporated herein by reference in their entireties. Alternatively, the catheter may be advanced to the desired site by means of a deflectable stylet, as disclosed in PCT Patent Application WO 93/04724, published Mar. 18, 1993, or a deflectable guidewire as disclosed in U.S. Pat. No. 5,060,660, issued to Gambale, et al., both of which patents are incorporated herein by reference in their entireties. When the hollow needle 3 is located at the desired location it is screwed into heart tissue by rotating the catheter body. A torque cable within the catheter body provides for 1:1 torque transfer from the proximal end of the catheter to the hollow needle 3.

When advanced to the desired location, Luer lock 7 is coupled to a pressurized source of Ringer's solution. An appropriate source is discussed in more detail in conjunction with FIG. 6 below. However, for purposes of the present invention, a source of Ringer's solution capable of delivering 2 cc per minute of solution at atmospheric pressure has been found to be adequate. Delivery of Ringer's solution should begin before or at the time at which the electrode 3 is screwed into the tissue to be ablated. In animal experimentation, the inventors have found that delivery of Ringer's solution for a period of two minutes prior to the delivery of RF energy assists in producing a larger but still controlled, regular lesion.

After the electrode has been located, and Ringer's solution has been administered for the desired period of time, electrical connector 8 is coupled to an RF electrosurgical power source. The present inventors have employed an Atakr™ RF Power Generator #0601, manufactured by Medtronic Cardio Rhythm. A prolonged application of RF energy, e.g., 50-watts for one minute or so, may be employed to produce a large, controlled lesion. Greater or lesser time periods may be employed, however time periods less than 20 seconds may be contra-indicated, as it appears that the cooling effect of the Ringer's solution, in such shorter RF application times, may actually decrease the effective size of the lesion.

The helical configuration of electrode 3 is believed to be particularly beneficial in the context of an ablation or hyperthermia electrode. Because the electrode is screwed into and completely located within the tissue to be ablatively or hyperthermically treated (i.e., out of the bloodstream), application of RF energy is limited to the tissue itself. This differs from traditional RF electrodes, which simply contact a tissue surface, with the result that a substantial portion of the energy applied is dissipated in the blood adjacent to the electrode site. Moreover, RF energy applied to the bloodstream may cause clotting of the blood adjacent the electrode, and raise the risk of clots breaking loose of the electrode.

The helical electrode also provides a substantially increased surface area as compared to the needle-like electrodes, and also serves to anchor the catheter reliably during application of the RF energy. In addition, the helical shape of the electrode prevents the application of conductive solution through the electrode from causing the electrode to be backed out of its insertion site due to hydraulic pressure, as might occur if a straight, hollow electrode were employed. The elongated path defined by the helical electrode also reduces the possibility of leakage of conductive fluid along the needle and out of the heart tissue.

FIG. 2 is a cross-sectional view of the distal end of the catheter illustrated in FIG. 1. In this view, it can be seen that helical electrode 3 is provided with an internal lumen 9 which is in communication with the internal lumen of a tube 10. Tube 10 extends to the proximal end of the catheter and is in fluid communication with Luer lock 5. As discussed above, tube 10 may be fabricated of polyimide tubing or of stainless steel tubing. In the present invention, the stainless steel tubing serves as an additional conductor, coupling electrode 3 to electrical connector 8 and enhancing the overall conductivity of the catheter. The use of polyimide tubing, while reducing the overall conductivity of the catheter, enhances the flexibility somewhat, and may be beneficial in some cases. It is recommended to apply a steady flow of Ringer's solution through the tubing to electrode 3 during passage catheter to the electrode site, if possible. The flow of Ringer's solution in this case assists in maintaining the patency of the lumen of tubing 10, and prevents plugging of the exit ports of the electrode as it is advanced into the cardiac muscle.

Figure 4:
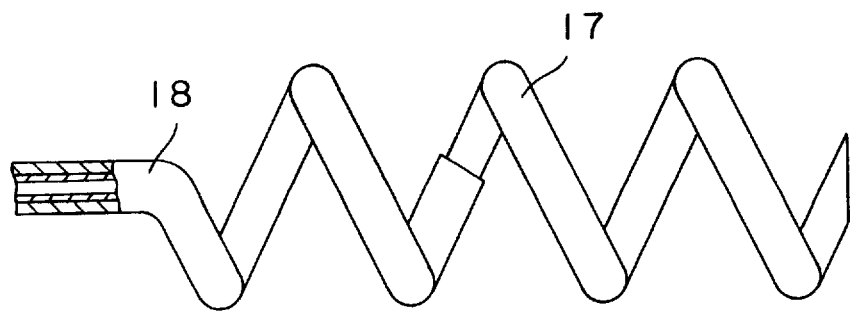
Figure 5:
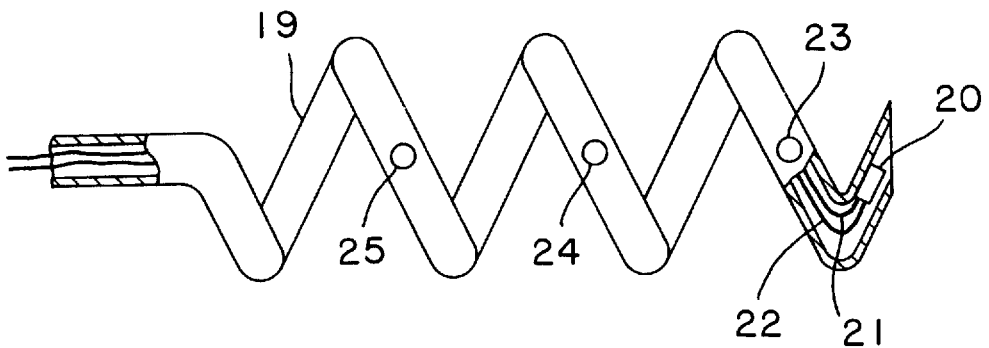

Surrounding tube 10 are two coils 11 and 12, which are wound in opposite directions, to provide a torque cable. In the case of the specific devices employed by the inventors, a torque cable as manufactured by Lake Region Manufacturing Company of Chaska, Minn. was employed, which torque cable is described in U.S. Pat. No. 5,165,421, incorporated herein by reference in its entirety. Coils 11 and 12 also serve as conductors. As illustrated, tubing 10 is between metal coils 11 and 12 and helical electrode 3. However, if polyimide tubing is used, the coils 11 and 12 will serve as the only conductor and thus will be electrically coupled to electrode 3 by means of welding, soldering or mechanical interconnection. Insulative sleeve 2 serves both to provide a smooth exterior for the catheter and to insulate the metal coils 11 and 12, along the length of the catheter FIGS. 3, 4 and 5 illustrate alternate embodiments of the helical electrode illustrated in FIG. 2. The electrode in FIG. 2 comprises a hollow tube having a single exit port located as its distal end. Electrode 13, illustrated in FIG. 3, corresponds to electrode 3 with the exception that additional exit ports 14, 15 and 16 have been added, allowing for dispensing of the Ringer's solution along the length of the helix. Ports 14, 15 and 16 may be laser drilled, and may be spaced in any desired fashion around the circumference of electrode 13 and along the length of electrode 13. Preferably, it is believed desirable to have ports spaced around the full circumference of the electrode, to provide for an even dispensing and dispersing of Ringer's solution.

Electrode 17, illustrated in FIG. 4, is a second alternative embodiment of a helical electrode corresponding to electrode 3, but with the addition of an insulative sleeve 18, which covers the proximal portion of the electrode. Sleeve 18 limits the application of RF energy to the distal portion of the electrode. Optionally, additional exit ports corresponding to ports 14, 15 and 16 illustrated in FIG. 3 may also be employed in conjunction with electrode 17. These additional exit ports may be limited to the exposed, uninsulated portion of electrode 17, or may extend along the entire length of electrode 17.

Electrode 19, illustrated in FIG. 5 is a third alternative embodiment corresponding generally to electrode 3. However, in this case, electrode 19 is provided with a thermocouple 20 located in the distal end of electrode 19. Thermocouple wires 21 and 22 extend backwards through the lumen within electrode 19 and are used to monitor the temperature at the tip of the electrode, for use in feedback control of power applied to the electrode as would be apparent to those of ordinary skill in the art. Only one of thermocouple wires 21 and 22 is insulated, and the other is simply coupled to the interior of electrode 19. In order to employ the electrode of FIG. 5, an additional electrical connector would have to be added, in order to allow connection to the thermocouple wire not connected to electrode 19. Alternatively, both thermocouple wires may be insulated, requiring two additional electrical connectors at the proximal end of the device, each coupled to one of the thermocouple wires. It should be noted that the thermocouple 20 effectively blocks the distal opening of the lumen within electrode 19, so that Ringer's solution will be dispensed only by means of side ports 23, 24 and 25.

Figure 6:
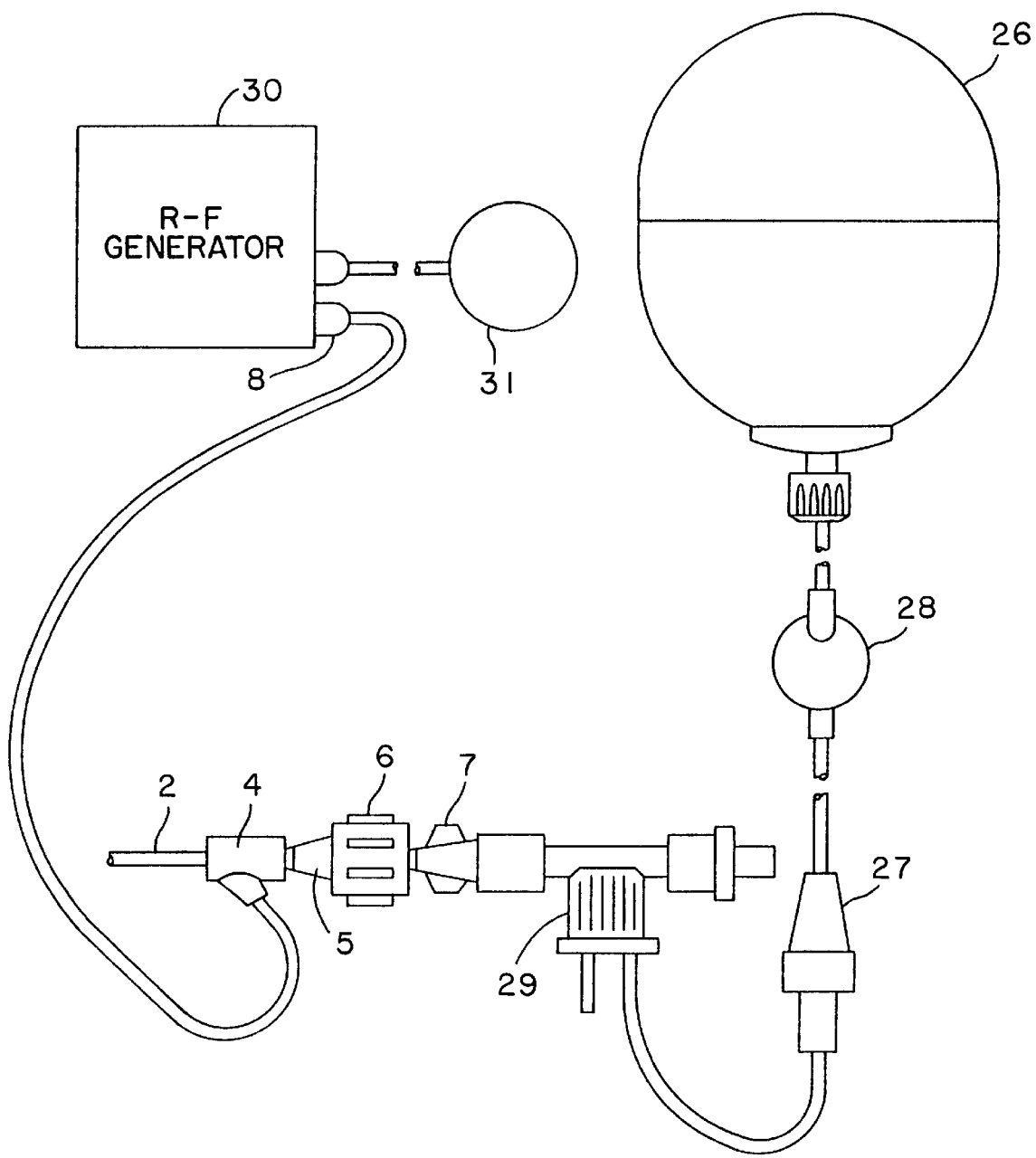
FIG. 6 illustrates the associated apparatus for administration of conductive solution before and during application of RF energy to the helical electrode.

FIG. 6 illustrates a pressurized source for Ringer's solution which may be employed in conjunction with catheter illustrated in FIG. 1. A reservoir 26 is provided, which is commercially manufactured by Block Medical Inc., and sold under the brand name "Home Pump". Reservoir 26 contains Ringer's solution and provides Ringer's solution at one atmosphere pressure to flow control 27, via filter 28. Flow control 27 may, for example, provide a flow limit of 20 drops or 1 cc per minute. Flow control 27 is coupled to a second flow control element 29, which, in the experimental apparatus employed by the inventors allows for additional adjustability of flow rates. Flow control 29 is coupled to the Luer lock 7, illustrated in FIG. 1, which in turn is in fluid communication with electrode 3 (FIG. 1), allowing delivery of Ringer's solution to the electrode. An electrosurgical generator 30 for providing RF electrical energy is illustrated in functional block form, coupled to electrical connector 8 and to a ground plate electrode 31 (not drawn to scale). All other labeled elements correspond to those illustrated in FIG. 1.

FIG. 7 illustrates a catheter employing a second, recessed electrode in addition to a penetrating, helical electrode 32 corresponding to electrode 3 as illustrated in FIG. 1. Electrode 32 protrudes out the distal end of the outer catheter sheath 33, which in turn is coupled to manifold 34, which includes a fluid fitting 35 and an electrical connector 36. Extending proximal to manifold 34 is a second manifold 37, preferably mounted rotatably with regard to manifold 35, and carrying a second fluid coupling 38 and a second electrical connector 39. Electrical connector 39 is coupled to electrode 32, and corresponds to electrical connector 8 of the device illustrated in FIG. 1. Fluid coupling 38 corresponds to Luer lock 7 illustrated in FIG. 1, and is employed to deliver Ringer's or other fluid to the interior of electrode 32.

FIG. 8 shows a cutaway view of the distal end of the catheter illustrated in FIG. 7, with the electrode 32 screwed into heart tissue 40. In this view, it can be seen that within the outer catheter tube 33 is a second catheter body 41, which may correspond precisely to the body of the catheter illustrated in FIG. 1, and includes an internal lumen fluid to the interior of electrode 32, as well as an electrical conductor, for coupling electrode 32 to electrical connector 39.

Mounted within outer catheter tube 33 is an internal, recessed electrode 42 which is coupled to electrical connector 36 by means of an insulated conductor 43. In use, electrode 32 is screwed into heart tissue 40, holding the distal end of outer catheter tube 33 tightly adjacent the tissue. Lumen 44 may then be filled with Ringer's solution, providing a conductive connection between the ring electrode 42 and the heart tissue 40. Electrodes 42 and 32 may be used individually or in conjunction with one another, to control the depth and shape of the lesion provided.

A typical lesion outline for the helical electrode 32 is illustrated by broken line at A, while a typical lesion outline for the recessed electrode 42 is illustrated at broken line at B. The lesions produced by recessed electrode 42 tend to be conically shaped, and located more closely adjacent the surface of the tissue. The lesions produced by electrode 32 tend to be more spherical or ovoid in configuration, and tend to be located deeper within the tissue.

Figure 9:
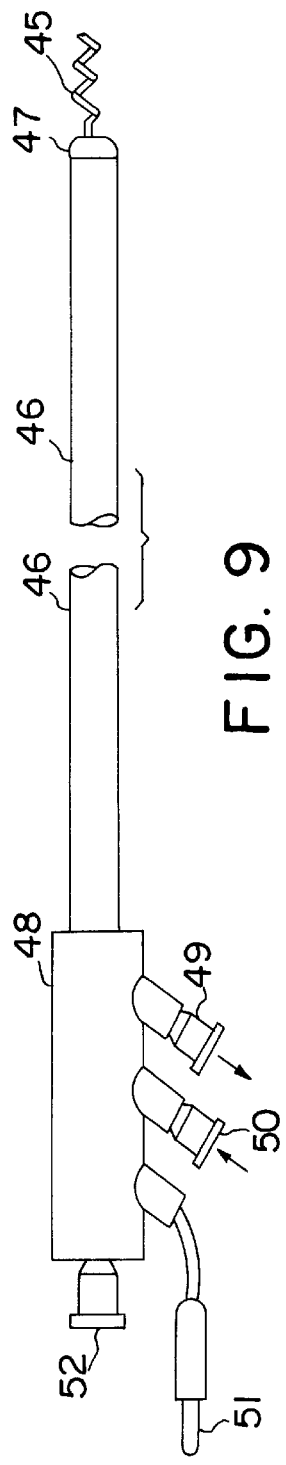
FIG. 9 illustrates an ablation or hyperthermia catheter in accordance with another alternative embodiment of the invention, adapted to deliver a chilled fluid to its helical electrode.

FIG. 9 illustrates embodiment of a catheter particularly adapted for use in delivery of a chilled fluid through its helical electrode 45. The catheter is provided with an elongated outer catheter tube 46, which terminates in a molded plastic member 47, from which the helical electrode 45 emerges. At its proximal end, a manifold 48 is coupled to outer catheter tube 46 and is provided with fluid couplings 49 and 50, for the ingress and egress, respectively, of a cooling fluid. Manifold 48 is also provided with an electrical connector 51 which is coupled electrically to helical electrode 45 and with a fluid coupling 52 which is coupled to the interior of electrode 45, and is used to deliver Ringer's solution through electrode 45.

Figure 12:
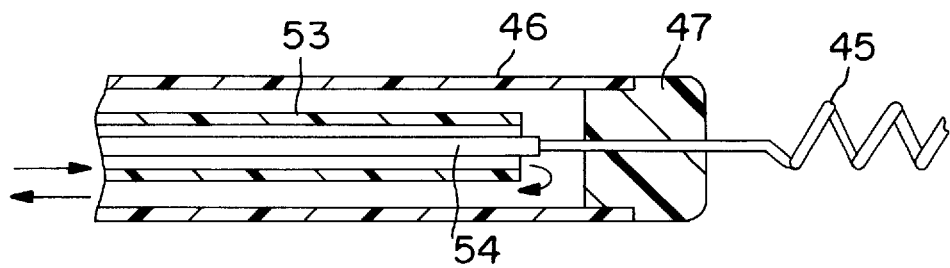
FIG. 12 is a cut-away view of the distal portion of the catheter from FIG. 9.

A cutaway view through the distal portion of the catheter illustrated in FIG. 9 is shown in FIG. 12. In this view, it can be seen that located within outer catheter tube 46 are an inner catheter tube 53 and a metal tube 54, fabricated, for example of stainless hypodermic tube, which serves to electrically couple electrode 45 to electrical connector 51 and to provide a fluid pathway from fluid coupling 52 to the interior of electrode 45. Plastic member 47 seals the distal end of the catheter.

The inventors have determined that it is difficult to inject chilled Ringer's solution down the length of the catheter as illustrated in FIG. 1 and FIG. 2, without the chilled solution becoming substantially warmed by the time it reaches the helical electrode. As a result, as illustrated in FIG. 12, the inventors have derived a catheter which provides for three fluid flow channels, arranged concentrically. The inner channel, defined by the hypotubing 54 serves to deliver the Ringer solution to the tissue, through electrode 45. The second fluid pathway, defined by the space between the inner tubing 53 and the hypotubing 54, is coupled to fluid coupling 50, which in turn is to be coupled to a pumping means for pumping chilled saline or other cooling fluid down the catheter body, through this intermediate lumen, in order to keep the Ringer's solution within hypotube 54 in a chilled state. At the distal end of the catheter, the cooling fluid leaves the intermediate lumen and enters the outer lumen defined by the space between outer catheter tube 46 and inner catheter tube 53, where it travels back up the catheter proximally, to fluid coupling 49, for recirculation. A pressurized source for Ringer's solution to be injected into the tissue is illustrated in FIG. 6, and would be coupled to fluid fitting 52, illustrated in FIG. 9. Any appropriate pumping mechanism may be used to deliver cooling fluid to fluid coupling 50 and to remove it from fluid coupling 49.

For purposes of mapping, it is preferred that the fluid delivered to the helical electrode 45 and injected into the tissue be no less than 1° C. In order to accomplish this, the temperature of the coolant fluid applied to fluid coupling 50 should be adjusted. If desired, a thermocouple, as discussed above, might optionally be employed in conjunction with electrode 45, and employed for temperature controlled regulation of the coolant temperature, as well as for temperature based feedback regulation of our power applied to the electrode ablation.

Tissue mapping with the catheter of FIG. 9 is accomplished by screwing the electrode 45 into the tissue to be tested, followed by delivery of chilled Ringer's solution at 2 cc per minute in order to slow conduction through the tissue, and monitoring the electrical activity of the heart by means of electrode 45, through electrical connector 51 (FIG. 9), while the patient is undergoing an episode of spontaneous or induced tachyarrhythmia. If cooling of the tissue terminates the arrhythmia, the site is identified as an appropriate location for RF ablation.

Figure 10:
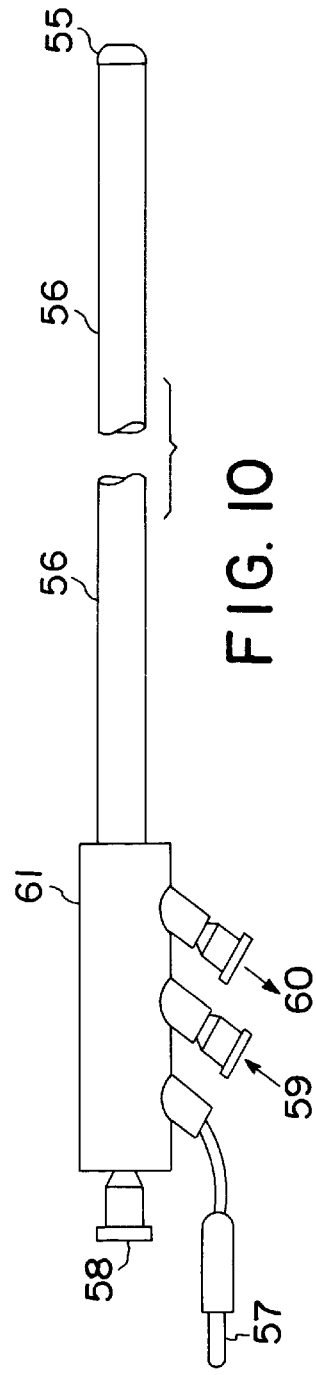
FIG. 10 illustrates an ablation or hyperthermia catheter in accordance with still another alternative embodiment of the invention, adapted to deliver a chilled fluid to a porous, non-helical electrode.
Figure 13:
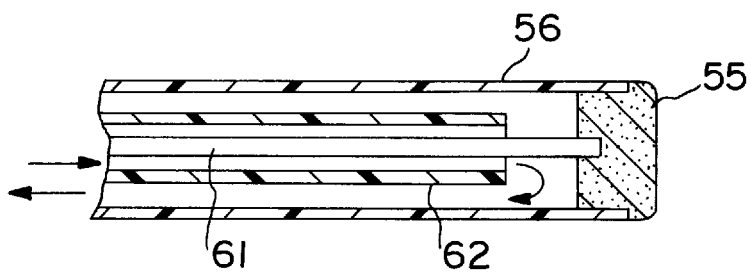
FIG. 13 is a cut-away view of the distal portion of the catheter from FIG. 10.

FIGS. 10 and 13 illustrate an alternative version of a mapping/ablation catheter differing from that illustrated in FIGS. 9 and 12 primarily in that rather than a helical electrode 45 (FIG. 12), a porous electrode 55 is provided, mounted to the distal end of the outer catheter tube 56. Porous electrode 55 is preferably fabricated by powder metallurgy techniques, similar to those described in conjunction with U.S. Pat. No. 4,506,680 to Stokes, and is provided with a porosity which provides a high resistance to fluid flow, for example 2-cc per minute at a pressure of 5-PSI. Electrode 55 is coupled electrically to electrical connector 57 and is coupled to a length of hypotubing within outer catheter body 56, which is in turn coupled to fluid coupling 58. Fluid couplings 59 and 60, on manifold 61 correspond to fluid couplings 49 and 50, mounted on manifold 48, in FIG. 9.

FIG. 13 shows a cutaway version through the distal portion of the catheter illustrated in FIG. 10, and in this view it can be seen that its internal structure is similar to that of the catheter illustrated in FIG. 13. A length of hypotubing 61 is coupled to electrode 55, providing both a fluid pathway to the electrode and an electrical connection to the electrode. Coolant enters the catheter through fitting 59, and flows down the catheter between inner catheter tube 62 and hypotube 61. Coolant exits the catheter flowing proximally between outer catheter tube 56 and inner catheter tube 62.

In the context of the present invention, the provision of a porous electrode 55 having a high resistance to fluid flow prevents the delivered chilled saline from simply leaking out and being washed away in the blood stream. By restricting the flow through the electrode, the electrode can be cooled to a degree which will allow its use for mapping purposes. The catheter may also be employed for ablation, with delivery of Ringer's solution through hypotube 61 being employed to prevent overheating of electrode 55 and to force conductive solution into the tissue, creating a virtual electrode in the wall. As in conjunction with the embodiments of the present invention employing helical electrodes, electrode 55 might also optionally be provided with a thermocouple, allowing for temperature control feedback of electrode temperatures during both mapping and ablation.

Figure 11:
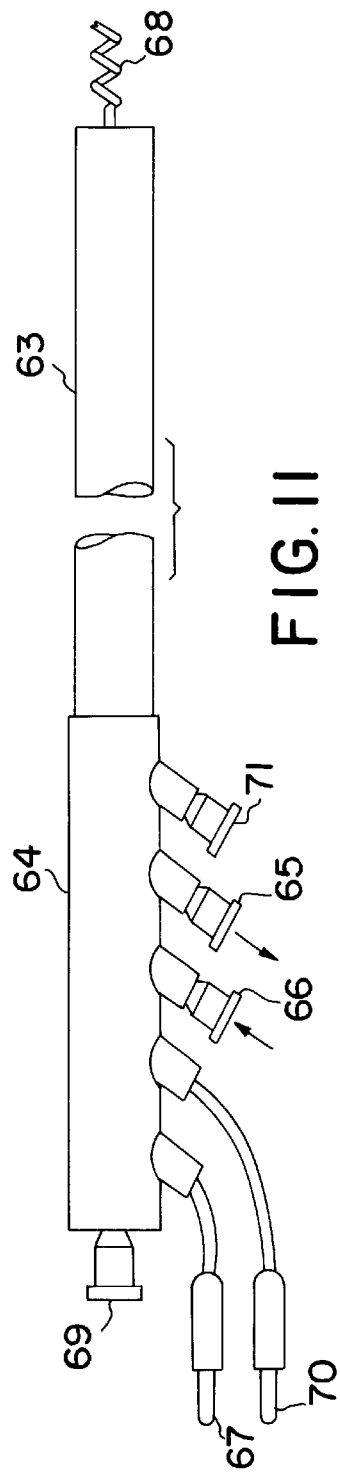
FIG. 11 illustrates an ablation or hyperthermia catheter in accordance with still another alternative embodiment of the invention, adapted to deliver a chilled fluid to a helical electrode and employing a second, recessed electrode.

FIG. 11 illustrates a second embodiment of a catheter, employing features of the catheters illustrated in FIGS. 7 and 9, in a single device. Outer catheter tube 63 carries a manifold 64 at its proximal end, which includes fluid couplings 65 and 66, for egress and ingress, respectively, of coolant. Electrical connector 67 is coupled to helical electrode 68. Fluid coupling 69 is coupled to the interior of electrode 68, allowing for delivery of Ringer's solution to the tissue, through electrode 68. Electrical connector 70 corresponds functionally to electrical connector 39 in FIG. 7, and is coupled to a recessed electrode located within outer catheter tube 63. Fluid coupling 71 corresponds functionally to fluid coupling 35 illustrated in FIG. 7, and serves to allow delivery of Ringer's solution within the outer catheter tube 63, in order to couple the recessed electrode tube, in the same fashion as discussed in conjunction with FIG. 8, above.

Figure 14:
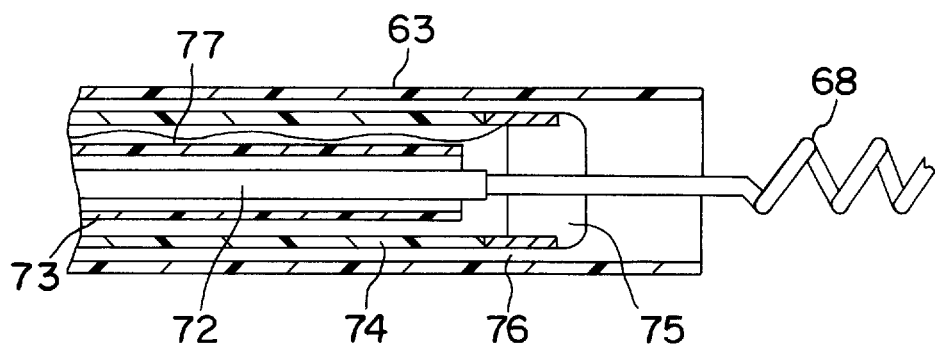
FIG. 14 is a cut-away view of the distal portion of the catheter from FIG. 11.

FIG. 14 is a cutaway view through the distal end of the catheter illustrated in FIG. 11. In this version of the invention, the catheter defines four concentric fluid paths. The innermost fluid path is defined by hypotubing 72 which is coupled to helical electrode 68. Ringer's solution is delivered from fluid coupling 69, through tube 72 to electrode 68. Tube 72 also is coupled to electrical connector 67. Mounted around tube 72 is inner catheter tube 73, which corresponds functionally to inner catheter tubes 53 and 62 as illustrated in FIGS. 12 and 13, respectively. Coolant flows distally through the catheter in the fluid space defined between inner catheter tube 73 and hypotube 72. Intermediate catheter tube 74 surrounds inner catheter tube 73, and the space therebetween defines the return fluid flow path for coolant fluid, which is in turn coupled to fluid coupling 65. Plastic member 75 corresponds to plastic member 55 in FIG. 13, and serves to seal the distal end of intermediate catheter tube 74. A ring electrode 76 is mounted around plastic member 75 and is coupled to electrical connector 70 by means of insulated conductor 77. The space between outer catheter tube 63 and intermediate catheter tube 74 defines the fourth, concentric fluid flow path, and is coupled to fluid coupling 71, allowing for injection of Ringer's solution into the interior of outer catheter tube 63, which in turn serves to couple electrode 76 to cardiac tissue, in the same fashion as discussed in conjunction with the catheter illustrated in FIGS. 7 and 8.

While the embodiment illustrated above requires a second element (e.g. a guide catheter or guide wire) for advancing and positioning the catheter at its desired location, it is anticipated that the basic apparatus disclosed above may also be incorporated into catheters which themselves are steerable or deflectable, similar to RF ablation catheters presently in clinical investigation. Similarly, it is anticipated that in commercial embodiments, alternative mechanisms (e.g. precision pumps) for controlling the flow of Ringer's solution may be employed. Similarly, while the inventors have employed Ringer's solution, other alternative fluids may be workable as well.

As previously noted, the above-referenced '441 application, (as well as the '246 and '304 applications) emphasize the applicability of the "fluid-assisted" ablation techniques to ablation of cardiac tissue. It is believed by the inventors, however, that the present invention may be advantageously practiced in connection with ablation and/or hyperthermic treatment of numerous other types of body tissue. The infusion of conducting solutions such as Ringer's, saturated saline, and the like, into the area of ablation or hyperthermia prior to and during the application of RF energy creates what is referred to herein as a "virtual electrode," the size and shape of which can be controllably modified, and which can be rendered more or less conductive, thereby modifying the spread of RF energy. The rate of infusion and conductivity of the perfusate can be controlled to work in conjunction with various electrodes with different surface areas. Different body tissues or tumors may require different sizes and shapes of electrodes for access and penetration. A smaller surface area metal contact electrode typically necessitates the use of a more conductive solution to effectively spread the energy and prevent desiccation at the electrode-tissue interface. By varying such factors as the RF energy and duration, the extent of pre-RF infusion, the RF infusion rate and conductivity of solution, the electrode size, shape, and surface area, the size, shape, and intensity of the "virtual electrode"—i.e., the intensity of thermal production in the ablation or hyperthermia area, can be controlled.

In prostate tissue, one application for which the present invention is believed to be well-suited, cessation of growth or debulking may be desired to treat benign prostate hyperplasia (BPH). Thermocouples may be inserted near the perimeter of the ablation or hyperthermia area, where nerves responsible for erectile tissue function lie, and near the urethra, where nerves and muscle responsible for opening and closing of the urethra during urination lie. A catheter in accordance with the present invention may be inserted into the prostate either through an opening in the abdomen, transurethrally, or through the rectum. This allows prostate ablation without damage to nerves and muscle involved in impotence and incontinence.

The present invention also allows for ablation or hyperthermic treatment of nonhomogeneous masses that may be within homogeneous organs or tissue, such as in the prostate or breast. Infusion of conductive solution in tissue will infiltrate around an in between more dense or non-homogeneous masses, such that when RF energy is applied, those masses will be ablated. The present invention is also believed to be advantageously applicable to treatment of other organs, tissues, and tumors in the body that would benefit from ablation or hyperthermic treatment to inhibit growth, debulk, or simply cease function of a pathological state. Tissue or tumor sites for which the present invention is believed to be applicable include, without limitation: prostate, breast, brain, neck, lung, lymphoid regions, esophagus, gastric mass, pancreas, liver, small intestines, large intestines, colon, ovaries, testis, pelvic region, uterus, cervix, oral cavity, larynx, bladder, kidney, and muscle.

Various alternative embodiments of the present invention are contemplated as having qualities which render them effective in particular applications, as will be hereinafter described in further detail. In each of the embodiments to be described hereinbelow, it is believed that the present invention advantageously facilitates the treatment of areas heretofore considered inoperable.

One alternative embodiment of the present invention is depicted in FIG. 15. Specifically, shown in FIG. 15 is an access port 90 having a metal helical tip electrode 92 corresponding generally to electrode 14 from FIGS. 1 and 2 (or, alternatively, corresponding to electrodes 36, 46, or 48 from FIGS. 3, 4, and 5, respectively).

It has been recognized in the prior art that cancer cells are sensitive to elevated temperatures, and in particular, that hyperthermia may be advantageously combined with other cancer therapy modalities, including chemotherapy and radiotherapy. See, e.g., Steeves, "Hyperthermia in Cancer Therapy: Where Are We Today and Where Are We Going;" Bull. NY Acad. Med. (U.S.) vol. 68, no. 2, March–April, pp. 341–350; Oleson, "Progress In Hyperthermia?;" Int. J. Radiation Oncology, Biology, Physics, vol. 20, (1991) pp. 1143–44; Dudar et al., "Differential Response of Normal and Tumor Microcirculation to Hyperthermia," Cancer Research, vol. 44, February 1984, pp. 605– 612; and Jain, "Barriers to Drug Delivery in Solid Tumors," Scientific American, vol. 271, no. 1 (July 1994), pp. 58–65.

In view of the recognition of the synergistic combination of chemotherapy with local heating, access port 90 in FIG. 15 is intended to facilitate local chemotherapy and simultaneous RF ablation or heating of malignant or non-malignant tumors, in order to ablate, arrest growth of, or functionally kill the tumors. Hollow electrode 92 is used for intra-tumor drug delivery and simultaneous RF ablation and/or heating (hyperthermia). Electrode 92 also facilitates perfusion of fluid (e.g., chemotherapy agents, ionic conductive fluids, ablating chemicals, etc . . . ) at its tip to increase the local effect of the drug. At the same time, the drug increases the local conductivity and prevents desiccation of tissues surrounding the electrode before and during application of RF energy.

With continued reference to FIG. 15, access port 90 comprises a generally disk-shaped access port body 94 configured to be subcutaneously implanted in the general region of a site to be ablatively or hyperthermically treated. Access port body 94, which is also shown in isolation in the perspective view of FIG. 16, is preferably made of a rigid, biocompatible material. In accordance with conventional drug infusion port technology, access port body 94 defines a hollow interior chamber which is accessible via a pierceable septum 96 disposed on an upper face thereof. Embedded within the interior chamber of port body 94 is a conductive metallic (e.g., titanium) plate 98 defining a bottom inner surface of the port's inner chamber. Conductive plate 98, in turn, is electrically coupled to the electrical conductor within a lead 100 which projects radially outward from access port body 94. Lead 100 serves two purposes: to provide a conduit for the conduction of fluid injected into port body 94 to be expelled from one or more apertures in hollow needle 92, and to provide electrical coupling between plate 98 and needle 92.

Access port body 94 may also be provided with a plurality of suture holes 102 for allowing access port 90 to be secured to subcutaneous tissue, in accordance with conventional practice. In use, access port 100 is initially implanted using conventional screw-in lead techniques, wherein lead 100 is advanced to the desired site, e.g., a tumor. Lead 100 may be guided to the desired location by being passed down a steerable or guidable catheter, as disclosed for example in the above-referenced U.S. Pat. No. 5,030,204, or by means of a fixed-configuration guide catheter, as disclosed for example in the above-referenced U.S. Pat. No. 5,104,393, or by some other suitable means. When needle 92 is positioned at the desired site, it is screwed into the tissue by rotating access port body 94 and lead 100. A torque cable or the like may be disposed along the length of lead 100 to facilitate the screwing in of needle 92.

Next, access port body 94 is subcutaneously secured, with septum 96 facing out. It is contemplated that access port 90 may remain chronically implanted. In use, access port 90 is percutaneously accessed with a needle 104 which pierces the patient's skin and septum 96 and which is inserted completely into the hollow interior chamber of access port body 94 in order for the distal tip of needle 104 to come into contact with plate 98. Needle 104 is preferably insulated, e.g., with a Teflon coating, except at its distal end.

A proximal assembly 106 of needle 104 is provided to facilitate introduction of fluid through needle 104 into access port body 94, and further to facilitate the electrical connection of an external RF generator (not shown in FIG. 15) to needle 104 and hence to plate 98. In this way, at the same time as fluid is being injected through needle into access port body 94 and along lead 100 to be expelled through apertures in needle 92, RF energy may be conducted along needle 94 to plate 98 and along the conductor of lead 100 to needle 92.

Figure 17:
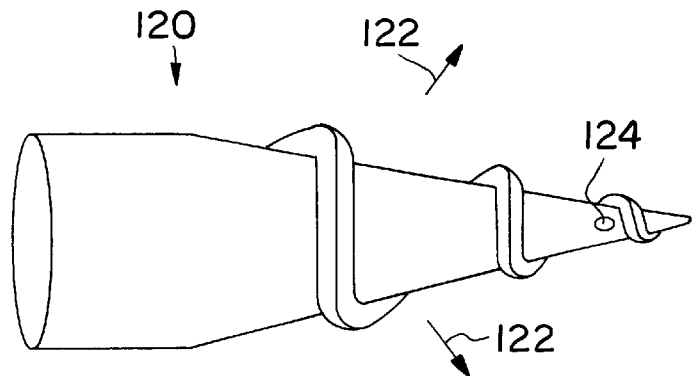
FIG. 17 is a side view of an alternative hollow, conductive needle for performing fluid-assisted ablation or hyperthermia in accordance with one embodiment of the invention.

Turning now to 17, there is shown an alternative embodiment of a tip electrode 120 for use in conjunction with the fluid-assisted ablation or hyperthermia catheters in accordance with the present invention. It is contemplated that tip electrode 120 may be used in conjunction with any of the embodiments disclosed in the above-referenced '441 '246 and '304 applications, as well as with the access port 90 described above with reference to FIGS. 15 and 16, not only for cardiac ablation, but also for intra-tumor ablation or heating. Electrode 120 is hollow to allow for perfusion of conductive solutions surrounding electrode 120 before and during ablation. Electrode 120 in FIG. 17 has a generally "wood-screw" shape, i.e., a conical shape, which creates pressure against tissue into which it is screwed, as indicated by arrows 122 in FIG. 17. A fluid port 124 is provided generally near the distal end of needle 120 to allow fluid to be expelled at a point beyond the seal between needle 120 and surrounding tissue. This prevents fluid from escaping in the proximal direction with respect to needle 120, keeping the fluid localized in the area of needle 120.

Figure 18:
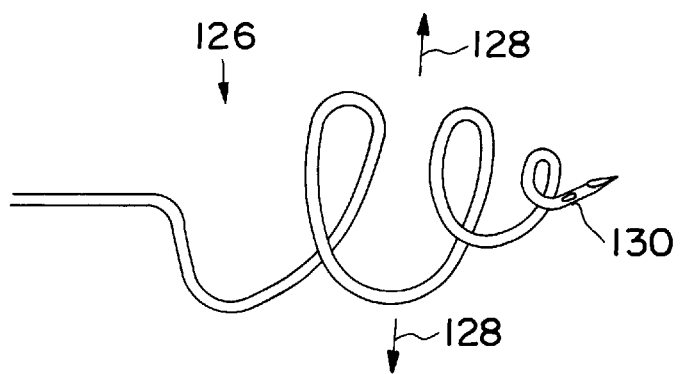
FIG. 18 is a side view of an alternative hollow, conductive needle for performing assisted ablation or hyperthermia in accordance with one embodiment of the invention.

In FIG. 18 there is shown still another alternative embodiment of a hollow needle 126 suitable for the purposes of fluid-assisted ablation in accordance with the principles of the present invention. Hollow needle 126 has an expanding helical shape which, when screwed into tissue (e.g., a tumor) tends to compress the surrounding tissue in the direction of arrows 128, thereby sealing off fluid leakage along the needle shaft. Fluid is ejected from needle 126 via a fluid port 130 disposed generally near the distal end thereof. Again, the compression of surrounding tissue against needle/electrode 126 is believed to be desirable, as it keeps the fluid localized with respect to needle 126, allowing for better control of the region of perfusion established for fluid-assisted ablation in accordance with the present invention.

Figure 19:
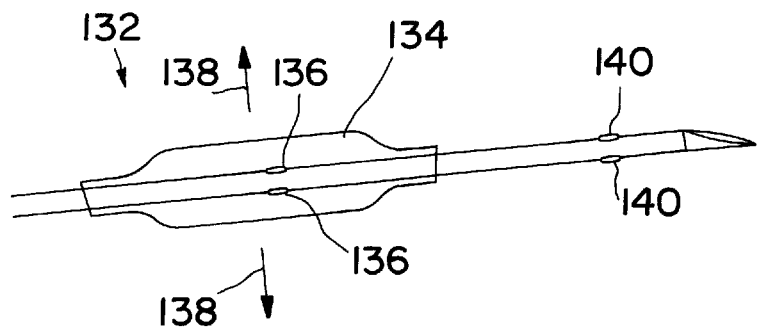
FIG. 19 is a side view of an alternative hollow, conductive needle and sealing balloon for performing fluid-assisted ablation or hyperthermia in accordance with one embodiment of the invention.

In FIG. 19 there is shown yet another alternative embodiment of a hollow needle 130 for performing fluid-assisted ablation or hyperthermia in accordance with the present invention. The embodiment of FIG. 19 comprises a hollow needle 132 having a small, circumferentially disposed balloon 134 spaced proximally back from the distal end thereof. Proximal apertures 136 in needle 132 function to allow fluid injected through needle 132 to expand balloon 134 after needle 132 has been inserted into the tissue to be treated. This causes compression of surrounding tissue in the direction of arrows 138, thereby preventing proximally-directed fluid leakage along the needle shaft. Distal apertures 140 allow for perfusion of the tissue to be treated, in accordance with the principles of the present invention. The very small diameter of the embodiment of FIG. 19 prior to inflation of balloon 134 (on the order of 1 French or so) is believed to be especially advantageous, and may facilitate the usefulness of the present invention for treatment of brain tumors.

Figure 20:
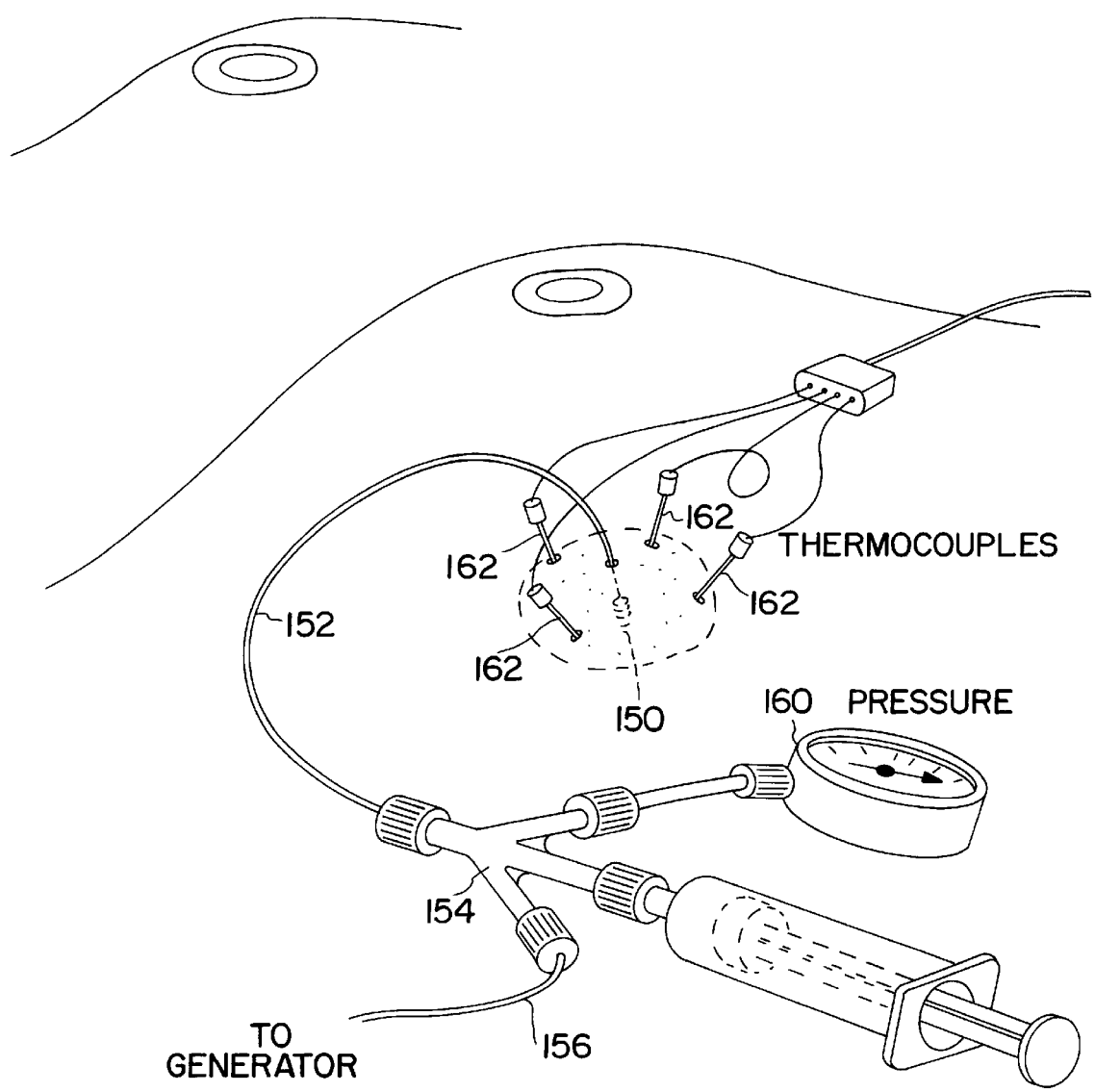
FIG. 20 is a perspective view illustrating a breast tumor fluid-assisted ablation or hyperthermia procedure in accordance with the present invention.

To further illustrate the applicability of fluid-assisted ablation or hyperthermia apparatuses and techniques in accordance with the present invention, FIG. 20 depicts a fluid-assisted ablation or hyperthermia procedure using a hollow needle/electrode for the heating of a breast tumor. FIG. 20 shows needle/electrode 150 disposed on the distal end of a fluid and electrically-conducting lead 152, with needle/electrode 150 having been inserted into a subcutaneous location at the site of a breast tumor. It is contemplated that needle/electrode may be of any of the configurations described herein, including those of FIGS. 1–5, 15, 17, 18, or 19, although it is believed that due to the consistency of breast tissue, a straight needle/electrode such as depicted in FIG. 19 is preferable for breast tumor treatment.

With continued reference to FIG. 20, a fitting 154 is disposed at the proximal end of lead 152 to facilitate the connection thereto of a source of RF energy 156, a source of perfusion fluid 158 (in FIG. 20, a syringe is depicted, although a pump or other fluid source may be used), and a pressure sensor 160. Pressure sensor 160 is used to monitor the pressure of fluid as it is applied through lead 152 and needle/electrode 150 to the ablation site. Also shown in FIG. 20 are several thermocouples inserted at locations surrounding the implant site for the purpose of monitoring the temperature of tissue in the region of the area of ablation, in order to ascertain on a dynamic basis the extent of the "virtual electrode" established as a result of perfusing the ablation site with conductive fluid. In this way, the region of tissue being ablated can be carefully monitored, and the RF energy and/or the pressure of conductive fluid modulated to control the extent of ablation. As previously noted, the extent of the "virtual electrode" can also be controlled through the selection of needle/electrodes having differing areas and differing configurations of fluid ports therein.

Figure 21:
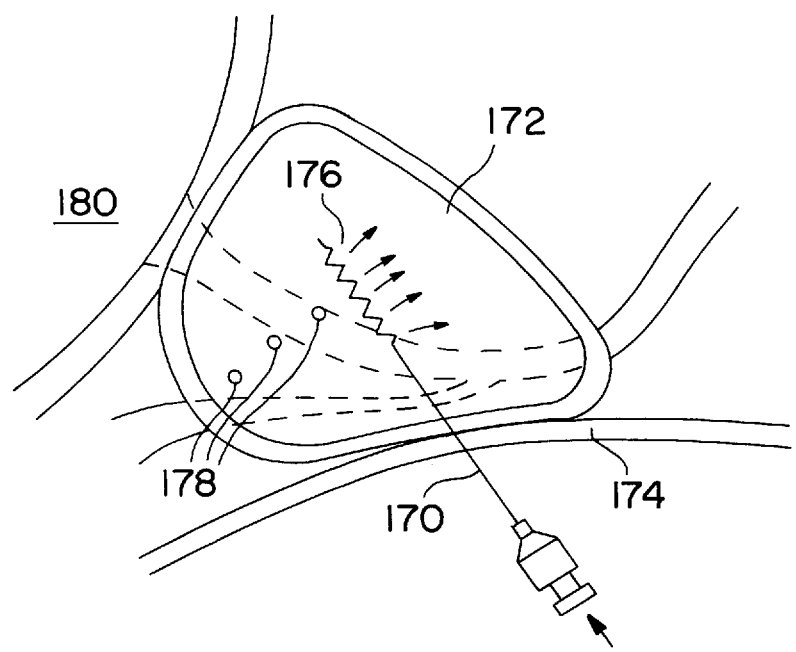
FIG. 21 is a cross-sectional view of a human prostate and surrounding tissue undergoing fluid-assisted ablation or hyperthermia in accordance with one embodiment of the invention.

In FIG. 21, there is shown an example of the present invention being practiced in connection with the ablation or hyperthermic treatment of prostate tissue. In particular, FIG. 21 shows a hollow, helical electrode/needle 170 inserted into the prostate 172 through the rectum 174. (It is contemplated that a fluid-assisted needle/electrode in accordance with the present invention can be inserted into the prostate either through an opening in the abdomen, transurethrally, or through the rectum, as depicted in FIG. 21.) In FIG. 21, electrode/needle 170 is of the helical type as described in the above-referenced '441 '246 and '304 applications, formed from small-diameter hypodermic tubing coiled in spiral fashion with several small holes formed along a distal section thereof. It is contemplated that other electrode configurations, as described herein, could also be utilized for prostate ablation. Preferably, a proximal section of the length of needle/electrode 170 is insulated, e.g., with Teflon, to restrict the delivery of RF energy to the prostate.

Figure 22:
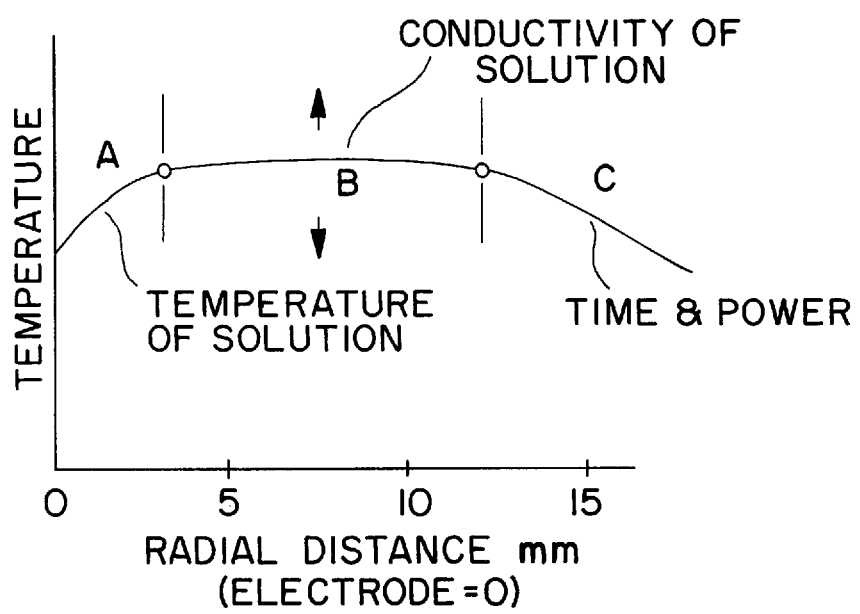
FIG. 22 is a temperature-versus-distance profile illustrating the thermal effects of fluid-assisted ablation or hyperthermia in accordance with one embodiment of the invention.

Prior to and during application of RF energy via electrode/needle 170, conductive fluid is injected through electrode/needle 170 at a slow rate to provide a conductive path or "virtual electrode" for RF energy into the tissue. The flow of fluid is represented by arrows 176 in FIG. 21. To illustrate the effects of such variables as RF power, time, conductivity of infused solution, temperature of solution, flow rate, and pressure upon the formation of the "virtual electrode," the profile of FIG. 22 is provided, wherein radial distance from electrode 170 is plotted along the horizontal axis and temperature is plotted along the vertical axis. The profile of FIG. 22 was experimentally obtained through placement of thermocouples 178 at 5-mm intervals from needle/electrode 176, as shown in FIG. 21.

What are believed to be among the unique characteristics of the profile of FIG. 22 as compared with prior art ablation systems are the relatively flat or constant temperature radially from the electrode, and the distance of effective heating achieved. It is believed that ablation and hyperthermia systems in accordance with the present invention renders possible the heating of areas as large as 4-cm in diameter. The temperature profile of FIG. 22 is divided into three main zones, designated A, B, and C in FIG. 22. Although multiple factors are reflected in each zone, what is believed to be the primary controlling element in each case is as follows:

The shape of the curve in zone A of FIG. 22 is affected primarily by the temperature of the conductive fluid infused through needle/electrode 170. The profile in zone B is affected primarily by the conductivity of the infused solution. As the solution conductivity decreases, the slope of the line increases with higher temperatures near the electrode. The relative temperature in zone B of the profile of FIG. 22 can be controlled by varying the conductivity of the infused solution, the rate of application of RF energy, and the length of time that RF energy is applied. Ablative temperatures have been reached using a mixture of 25% saturated saline and normal saline. Using such a mixture, a temperature difference in the range of 10° C. can be achieved.

With continued reference to FIG. 22, the temperature profile in zone C is affected by time, power, and the normal thermal and electrical conductivity of the surrounding tissue. For example, the bladder (designated 180 in FIG. 21) when filled with solution acts as a thermal and RF energy sink and the temperature curve in zone C falls steeply. This is believed to be a desirable condition since it acts to protect tissue surrounding the prostate 172 (e.g., the urethra) from being ablated. (It is believed that a modified Foley catheter placed in the urethra during an ablation procedure in accordance with the present invention, with a sterile, conductive, cooled solution circulating through it, should act as a further thermal and electrical sink protecting the urethra while allowing structures around it to be ablated.)

Figure 23:
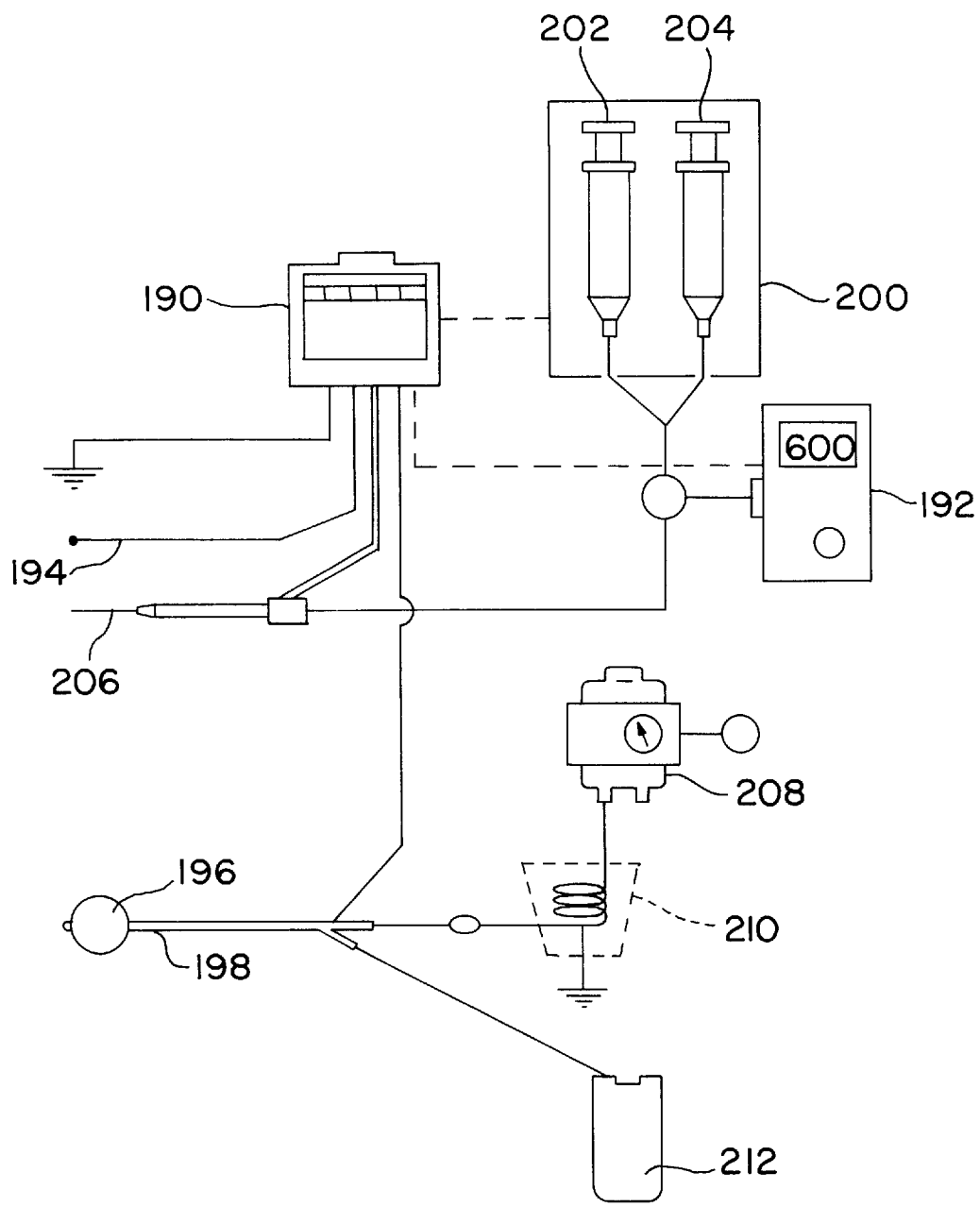
FIG. 23 is a schematic diagram of a fluid-assisted ablation/hyperthermia apparatus in accordance with one embodiment of the invention.

The complete system used to perform the prostate treatment as depicted in FIG. 21 is shown in FIG. 23. An RF generator 190, for example, a commercially-available CardioRhythm generator, may be used, although generator 190 is preferably modified to accept additional monitoring inputs, including a pressure monitor 192, a remote thermocouple 194, and a thermocouple 196 placed inside a urethral cooling catheter assembly 198. A small proportioning pump, for example, a dual syringe pump 200, is used to proportion normal saline 202 and saturated saline 204 solutions, and to deliver to hollow-needle electrode 206 in accordance with the present invention. Pressure monitor 192 is preferably included to send an alarm to generator 190 in the event that the infusion level falls below a preset level indicating failure of the virtual electrode. Sterile saline 208 is pumped through a heat exchanger (ice bucket) 210 and through a urethral cooling catheter assembly 198. Drainage 212 from the urethral cooling assembly 198 is also provided.

Figure 24:
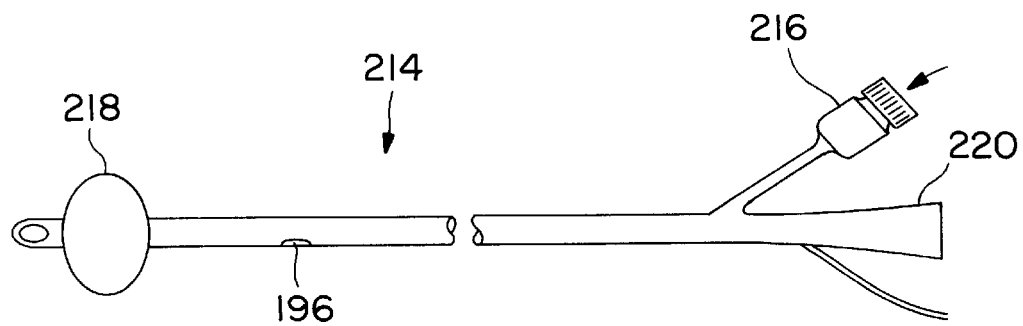
FIG. 24 an illustration of one component from a urethral infusion catheter used in conjunction with the apparatus of FIG. 23.
Figure 25:
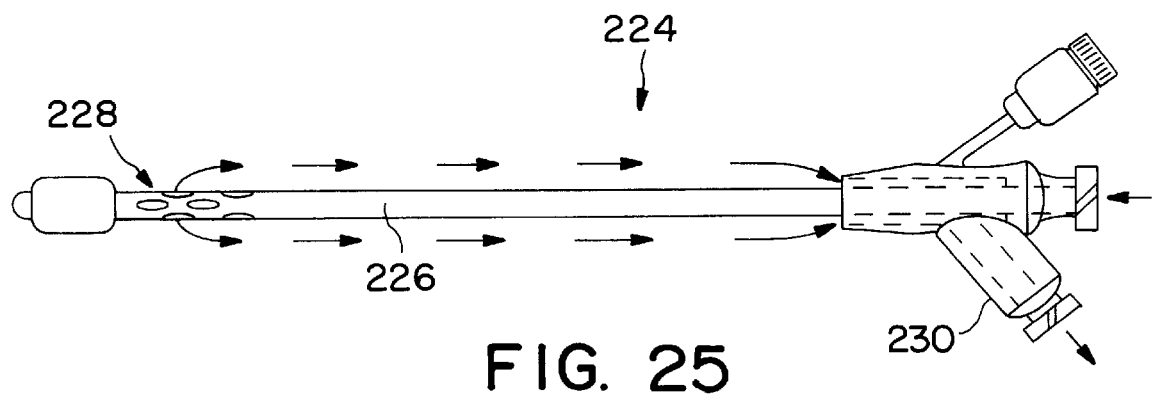
FIG. 25 is an illustration of another component from the urethral infusion catheter from FIG. 24.

Urethral cooling catheter assembly 198 is shown in greater detail in FIGS. 24 and 25. FIG. 24 shows a modified Foley catheter 214 having a port 216 for inflation of distal balloon 218 and a drain port 220. Also shown in FIG. 24 is thermocouple 196 and the lead 222 for coupling thermocouple 196 to RF generator 190. After Foley catheter 214 is placed in the urethra, an infusion stylet 224 shown in FIG. 25 is inserted into the lumen thereof. Sterile conductive solution flows from the reservoir 208 (see FIG. 23), through heat exchanger 210 and into the central lumen 226 of infusion stylet 224. The solution flows through central lumen 226 of infusion stylet 224, escapes from holes 228 in the distal end thereof, and then flows retrograde inside catheter 214 (FIG. 24) around central lumen 226 and exits out of connector 230 into drain 212. After the ablation procedure, infusion stylet 224 is removed and catheter 214 is left in place to function as a normal Foley catheter, if desired.

The exterior surface of catheter 214 may be treated with coatings to reduce the possibility of bacterial infection as well as to prevent adhesion to the urethra. Thermocouple 196 in catheter 214 can allow the system to shut down if temperatures in the urethral wall exceed a desired level.

Figure 26:
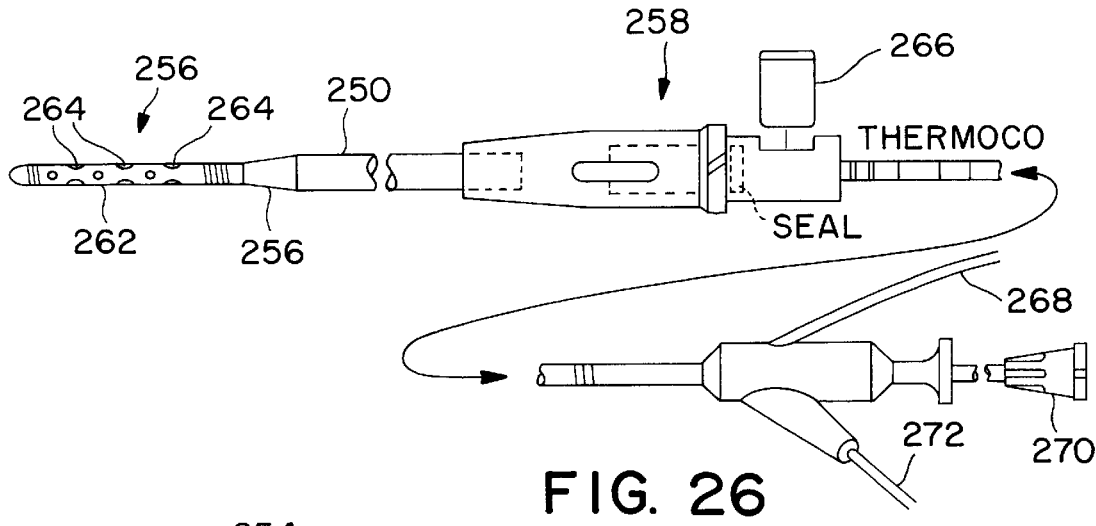
FIG. 26 is an illustration of an alternative embodiment of a catheter for fluid-assisted ablation or hyperthermia in accordance with the present invention.
Figure 27:
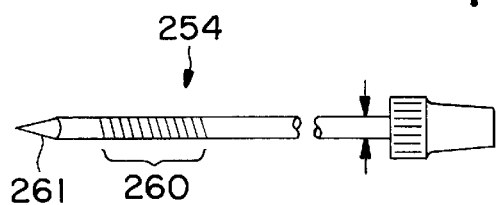
FIG. 27 is an illustration of an introducer stylet for use in introducing the catheter of FIG. 26 to perform fluid-assisted ablation or hyperthermia in accordance with the present invention.
Figure 28:
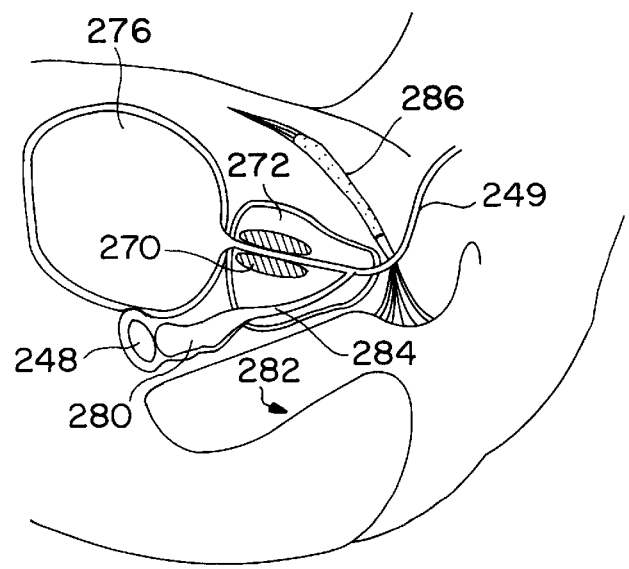
FIGS. 28, 29a, 29b, 30, and 31 are illustrations of a human prostate and surrounding tissue at progressive stages of a fluid-assisted ablation procedure in accordance with the present invention using the apparatus from FIG. 23.
Figure 29A:
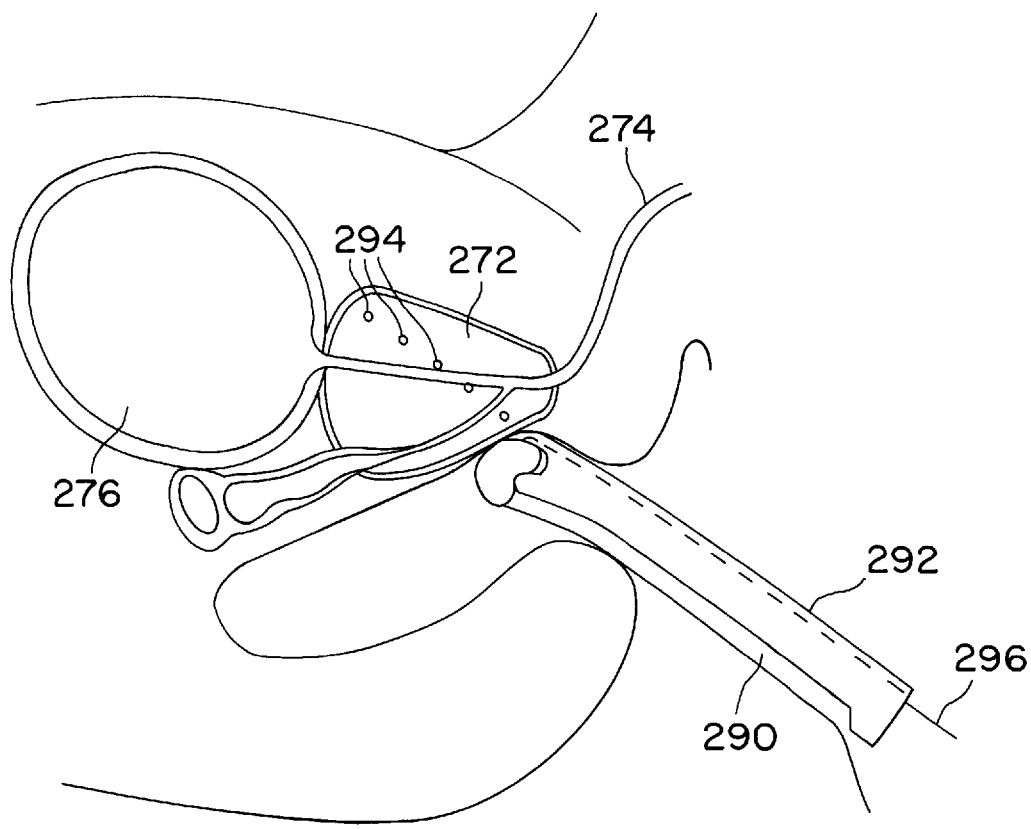
Figure 29B:
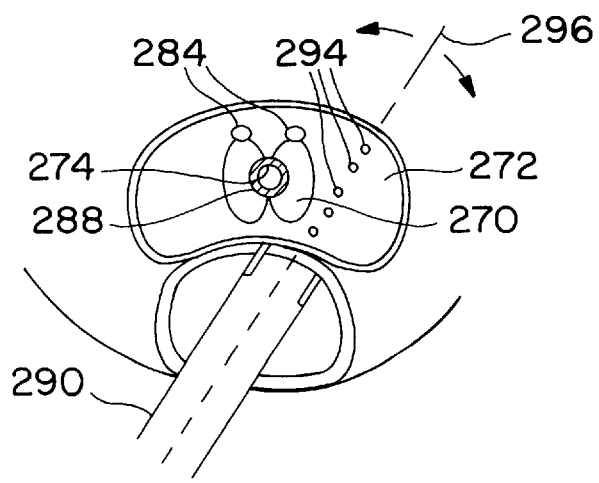

Needle/electrode 206 in accordance with one embodiment of the invention is shown in FIG. 26. Needle/electrode 206 comprises three main parts: an outer sheath 252; an introducer stylet 254 (shown in FIG. 27); and an electrode assembly 256. In the presently preferred embodiment, outer sheath 252 is 20-cm long and consists of an 18-gauge Teflon or polyurethane sheath with a tapered distal end 256 and a Luer lock fitting 258 on its proximal end. Sheath 252 insulates electrode assembly 256 from the rectal wall and other surrounding tissue. Introducer stylet 254 is placed through sheath 250 in order to introduce sheath 250 through the rectal wall and into the prostate. Stylet 254 has a series of rings 260 formed near its distal end for location of the needle-like distal end 261 thereof under ultrasound imaging, for example, as described in U.S. Pat. No. 4,582,061 to Fry.

Electrode assembly 256 comprises a 19-gauge cannula 262 closed at its distal end and having a series of small holes 264 along the distal 2-cm thereof. The proximal end of electrode assembly 256 has a depth stop 266 for allowing the physician to expose up to 2.5-cm length of the distal end of electrode assembly beyond sheath 250, in order to match the size of the exposed electrode portion to the size of the area to be ablated. The proximal end of electrode assembly also has a thermocouple connection 268, a conductive solution input connection 270, and an RF power connection 272.

Having described one embodiment of a fluid-assisted ablation catheter system in accordance with the present invention with reference to FIGS. 21–27, a preferred method of use of the catheter will now be described with reference to FIGS. 28–31, in which the reference numeral designations are as follows:

| ELEMENT | REFERENCE NUMERAL |
|---|---|
| Thermocouple | 194 |
| Transition zone | 270 |
| Prostate | 272 |
| Urethra | 274 |
| Bladder | 276 |
| VAS Deferens | 278 |
| Seminal vesicles | 280 |
| Rectum | 282 |
| Ejaculatory duct | 284 |
| Urogenital diaphragm | 286 |
| Urethral muscle | 288 |
| Ultrasound probe | 290 |
| Needle guide | 292 |
| Ultrasound dots | 294 |
| Needle | 296 |
| Notched biopsy needle | 298 |
| Biopsy sheath | 300 |
| Ablation fluid flow | 302 |

Needle/electrode 206 and remote thermocouple 194 are preferably placed transrectally by ultrasound guidance after obtaining a core biopsy in accordance with conventional surgical practice. As will be appreciated by those of ordinary skill in the art, hyperplasic nodules tend to form in a transition zone, designated with reference numeral 270 in the Figures, while cancer tends to occur in the outer regions of the prostate capsule, designated with reference numeral 272. The urethra 274 passes through the center of prostate 272, which in humans consists of two symmetrical lobes. A needle guide (designated with reference numeral 292 in FIG. 29a) is inserted as shown in the lateral view of FIG. 29a and the rectal view of FIG. 29b. As guide 292 is moved from side to side the visualization plane can be located in either lobe of prostate 272. Those of ordinary skill in the art will appreciate that most ultrasound systems project a series of dots 294 spaced 0.5-cm apart to project the path of the needle and to provide depth markings for locating biopsy needles.

The first step in the ablation/hyperthermia procedure in accordance with the present invention is to locate the controlling thermocouple 194 at the edge of the area to be treated. An ultrasound probe 290 is pushed against prostate 272 and rotated until the correct path is achieved. A small gauge needle 296 with ultrasound markings (a "highlighter") is then introduced, through which thermocouple 194 is placed. Ultrasound probe 290 is then withdrawn and thermocouple 194 is pulled through needle guide 292.

Figure 30:
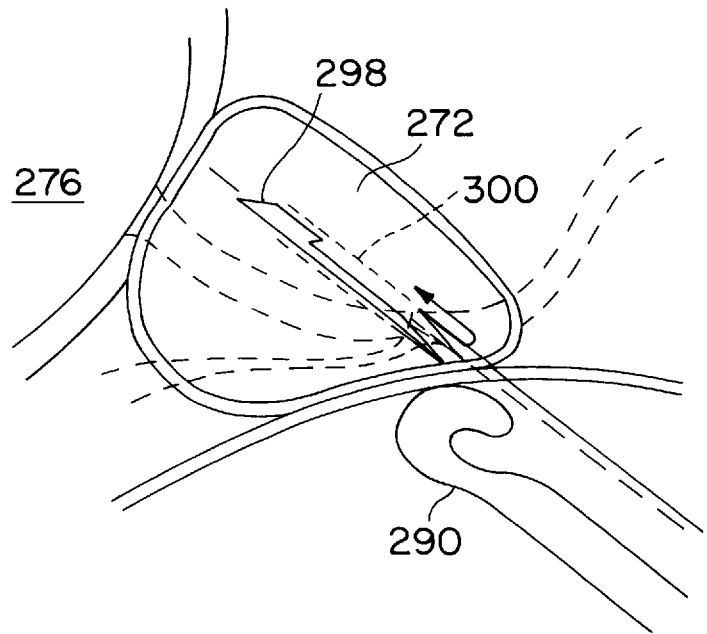

The next (optional) step is to perform a core biopsy procedure, as shown in FIG. 30. A frequently used system for the core biopsy procedure is the Bard biopsy system which uses a notched needle 298. Ultrasound probe 290 is placed against prostate 272 and rotated until the biopsy path is in the correct location. The biopsy gun fires the core biopsy needle 298 into the prostate followed almost immediately by advancement of a sheath 300, trapping the biopsy specimen between sheath 300 and needle 298. Needle 298 is then withdrawn for subsequent placement of electrode 206, for which the track formed by the biopsy can be used. Ultrasound probe 290 is preferably left in place.

Figure 31:
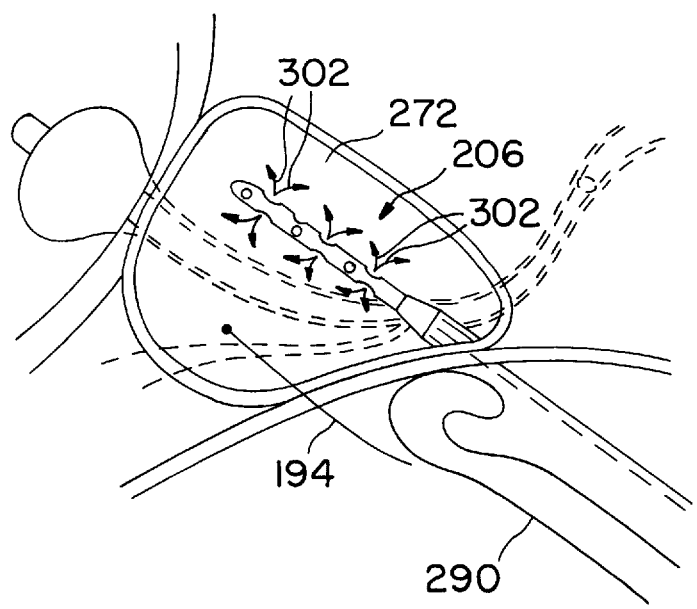

Next, electrode 206 is set to the proper length and is introduced through needle guide 292, as shown in FIG. 31. Conductive fluid infusion, represented by arrows 302 in FIG. 31, is started and continued for a time period proportional to the desired size of ablation. Lidocaine may be mixed with the solution to minimize any pain that might be incurred during this process.

Next, RF power is applied. The power of generator 190 is multiplexed with the ultrasound, so that the size of the lesion can be monitored. (See, e.g., Onik, "Percutaneous Transrectal Prostate Cryosurgery Using Transrectal Ultrasound Guidance: Animal Model," *Urology*, vol. 37, no. 3, p. 277 (March 1991); Masters, "Interstitial Laser Hyperthermia," *Seminars in Surgical Oncology*, vol. 8, pp. 242–249 (1992).

When thermocouple 194 indicates that the desired target ablation temperature, the system of FIG. 23 will turn off power to RF generator 190, and electrode 206 and thermocouple 194 can be withdrawn. The entire procedure can be performed in approximately five minutes. The process can be repeated for the second lobe of prostate 272.

Canine experimental data obtained in connection with a prostate ablation procedure as just described shows that the fluid-assisted ablation technique and apparatus in accordance with the present invention offers benefits over the prior art. FIGS. 32–38 show temperature profiles for experimental ablation procedures carried out under various conditions, as follows:

the energy is effectively distributed over a larger area, the shape and extend of which may be controlled through adjustment of various factors, including energy levels, rate of infusion, conductivity of infused liquid, etc . . . , as discussed above.

In the embodiments of the invention thus far described, the virtual electrode is created using a unipolar electrode configuration to deliver RF energy; that is, the electrode/needle is coupled to only a single (e.g., positive) terminal of an RF generator, and body fluid and tissue surrounding the ablation site (electrode) serve as the other (e.g., negative) electrode for the RF energy circuit. It is contemplated with a further aspect of the invention that bipolar, fluid-assisted ablation or hyperthermia may also be advantageously practiced.

Figure 39:
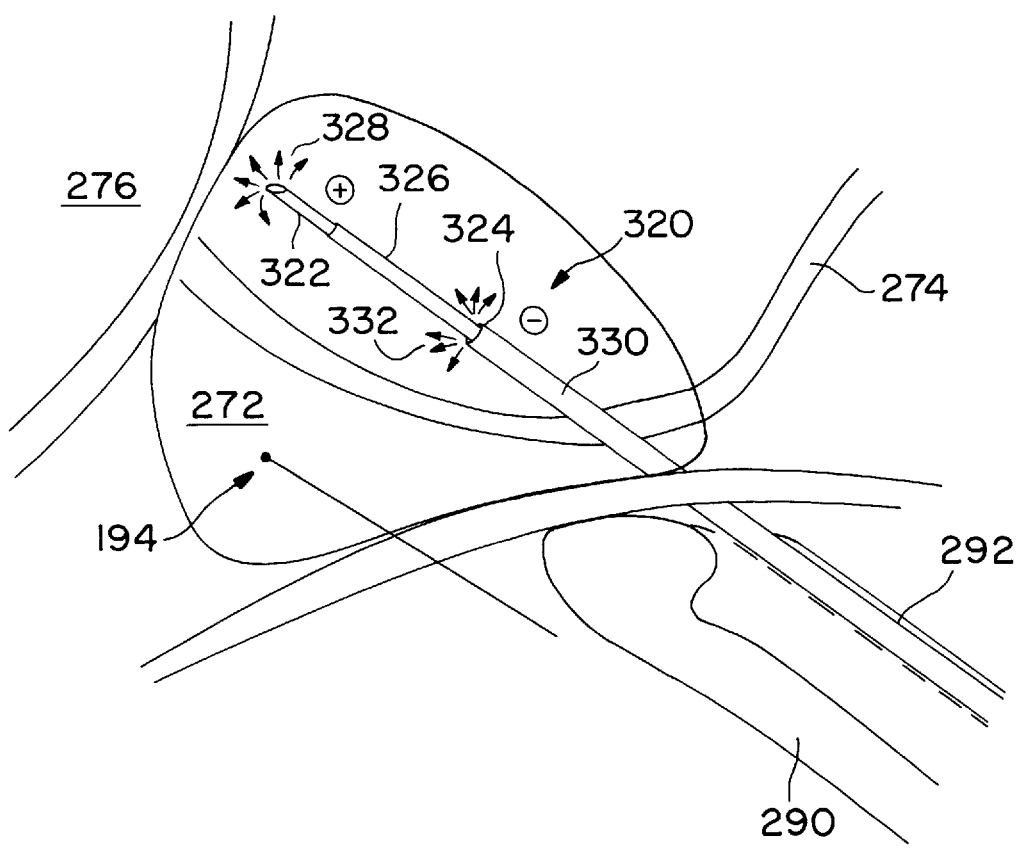
FIG. 39 is an illustration of a bipolar ablation/hyperthermia catheter in accordance with one embodiment of the invention, being used for prostate ablation.

In FIG. 39, there is depicted one embodiment of a bipolar ablation/hyperthermia catheter 320, inserted into prostate 272 using the same techniques as described above with reference to FIGS. 28–31. (In FIGS. 39–42, elements like prostate 272, urethra 274, bladder 276, ultrasound probe 290, needle guide 292, thermocouple 294, etc . . . which are identical to those described above with reference to FIGS. 28–31 have retained the same reference numerals.) In FIG. 39, bipolar catheter 320 is shown as having two electrodes: a first, designated with reference number 322 disposed

Figure 32:
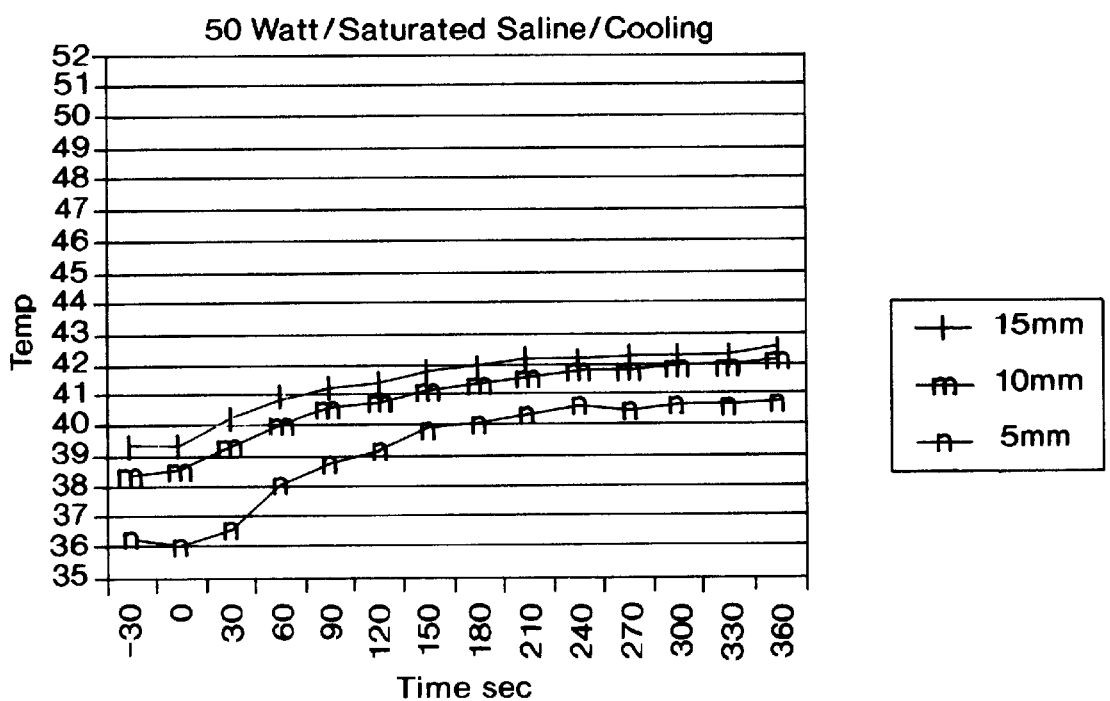
FIGS. 32–38 are temperature-versus-distance profiles illustrating experimental results of fluid-assisted prostate ablation in accordance with the present invention.
Figure 33:
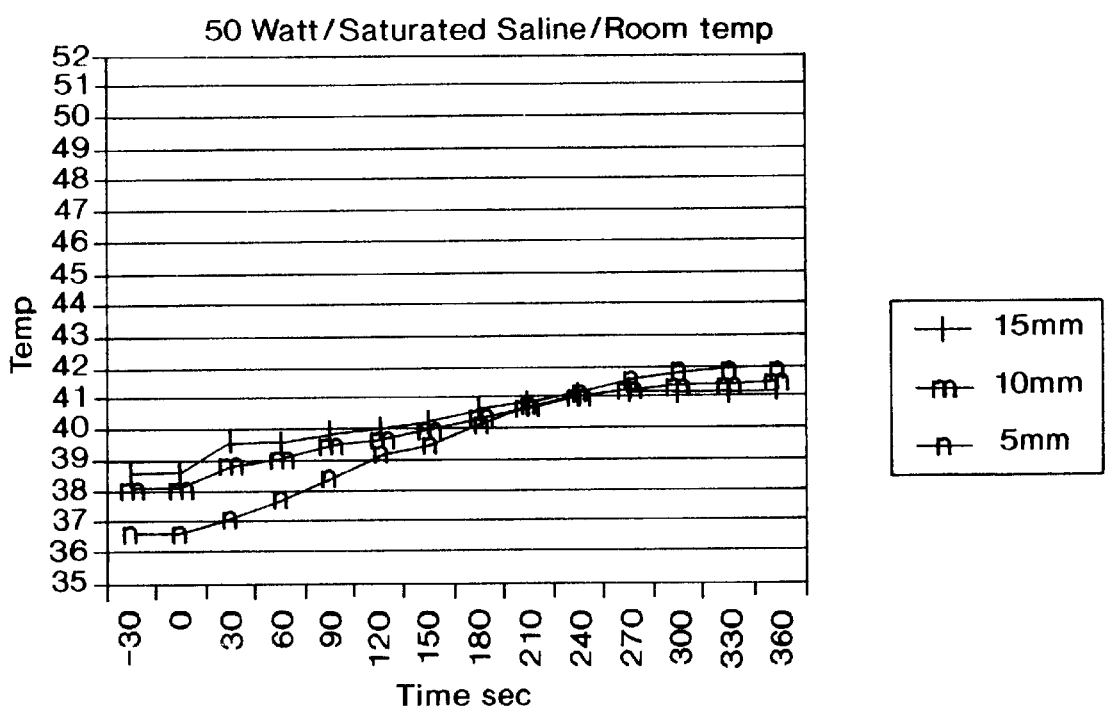
Figure 34:
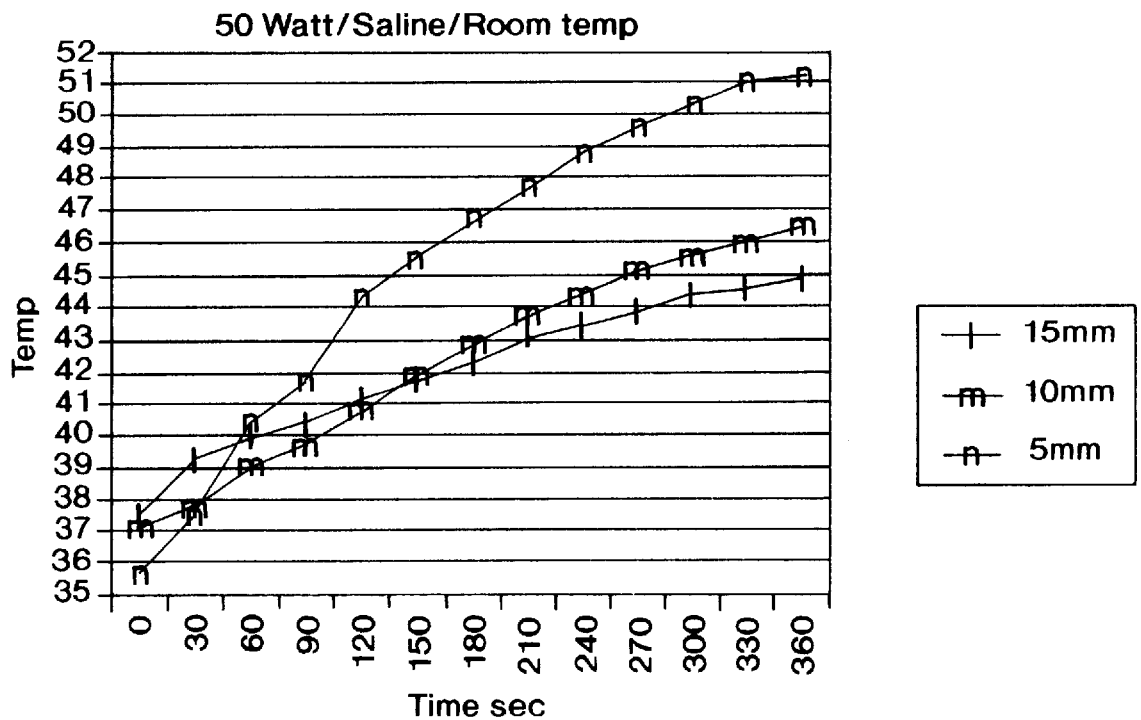
Figure 35:
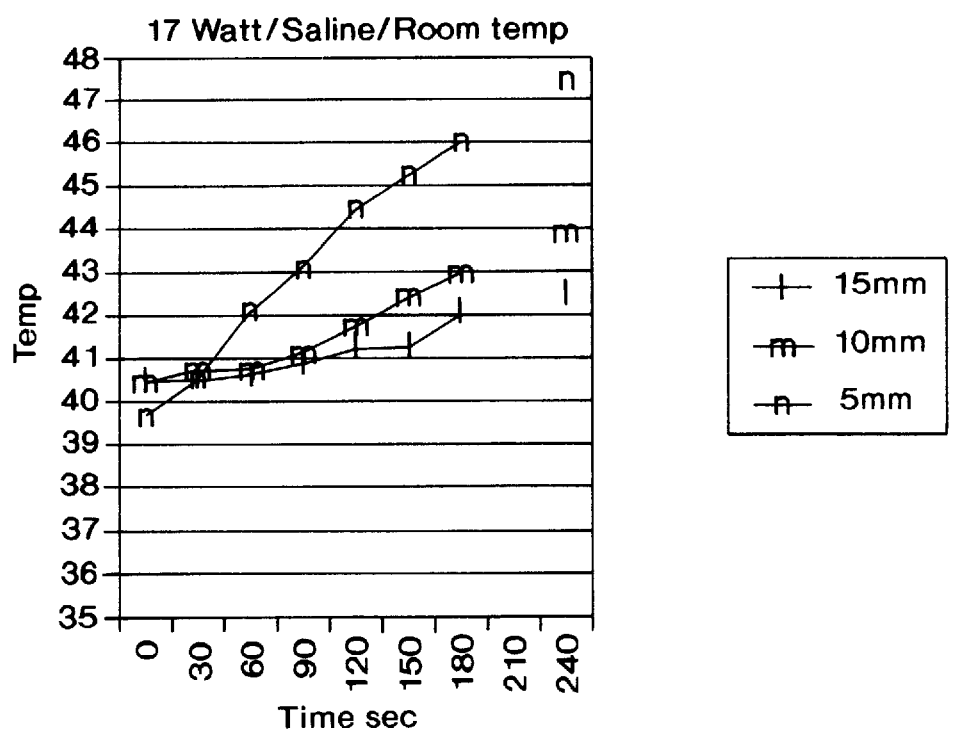
Figure 36:
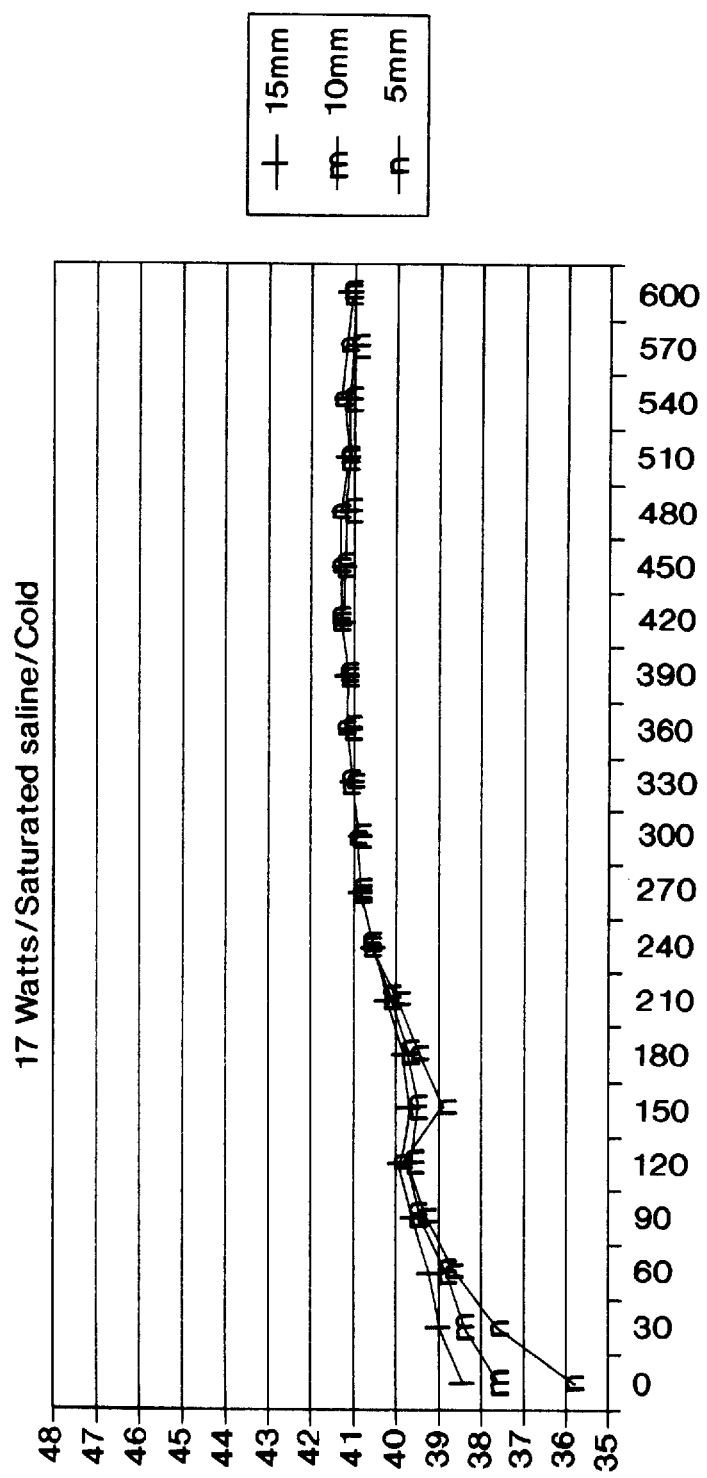
Figure 37:
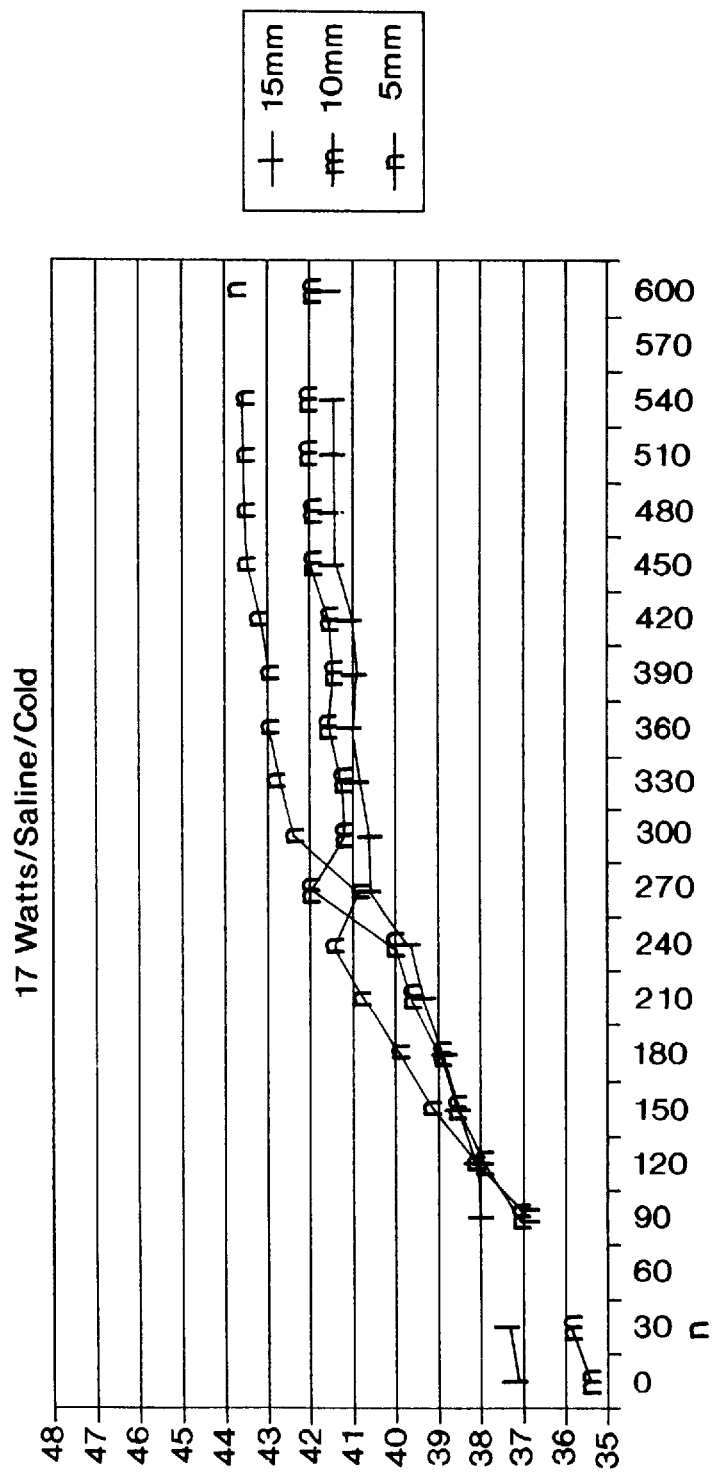
Figure 38:
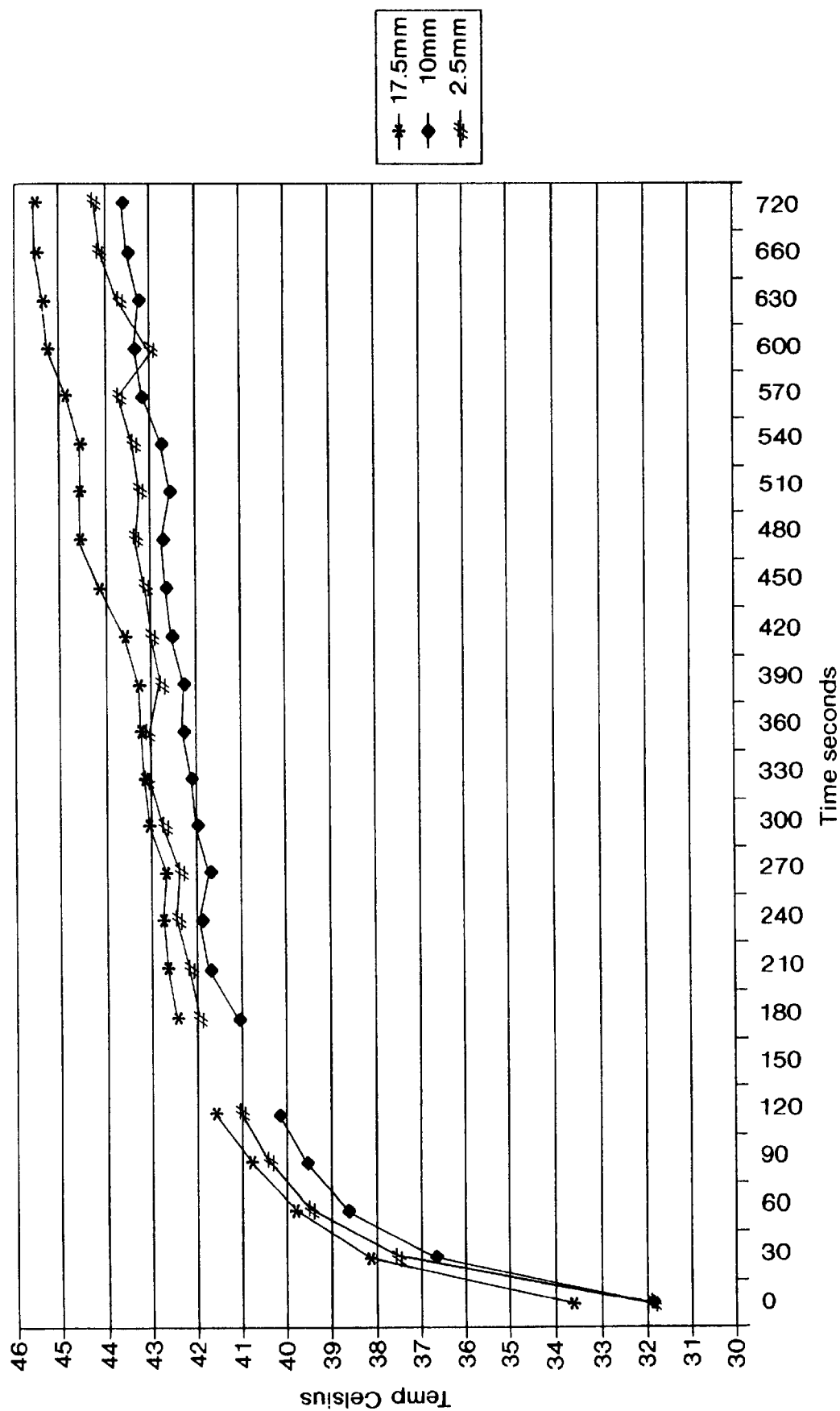

| FIG. NO. | ELECTRODE TYPE | RF POWER | SOLUTION TYPE | SOLUTION TEMPERATURE | THERMOCOUPLE DEPTH |
|---|---|---|---|---|---|
| FIG. 32 | 20-mm screw | 50 Watt | Saturated saline | Cooled | 7-mm |
| FIG. 33 | 20-mm screw | 50 Watt | Saturated saline | room temp. | 7-mm |
| FIG. 34 | 20-mm screw | 50 Watt | Saline | Room temp | 7-mm |
| FIG. 35 | 20-mm screw | 17 Watt | Saline | Room temp | 7-mm |
| FIG. 36 | 20-mm screw | 17 Watt | Saturated Saline | Cooled | 7-mm |
| FIG. 37 | 20-mm screw | 17 Watt | Saline | Cooled | 7-mm |
| FIG. 38 | 20-mm screw | 5 Watt | Saturated saline | Cooled to 6° C. | 12-mm |

In FIGS. 32–38, time in seconds is plotted along the horizontal axis, and temperature in degrees C is plotted along the vertical axis. From FIGS. 32–38, it will be apparent to those of ordinary skill in the art that, especially when the infusion solution is cooled, the method and apparatus in accordance with the present invention exhibit desirably constant ablation temperature increases throughout a relatively large ablation area.

It is believed that those of ordinary skill in the art will appreciate from FIGS. 32–38 the advantageous characteristics of the present invention in controllably establishing ablative or hyperthermic temperature gradients in prostate tissue. FIG. 33, for example, shows that with room-temperature saturated saline and 50-watts of RF energy for 360-sec, there is a temperature spread of approximately 1° C. between the 5-mm and 15-mm thermocouples. This demonstrates that the increased conductivity of the virtual electrode spreads the energy farther away from the metal electrode, thereby expanding the area of ablative or hyperthermic heating.

As noted above, it is an important aspect of the present invention, in each of the embodiments proposed herein, that delivery of fluid concurrently with the application of RF ablation energy creates a "virtual electrode" at the ablation site. Injection of the conductive liquid prior to and during the application of RF energy tends to decrease the current density of the RF energy in the immediate vicinity of the metallic (conductive) electrode. The current density at the periphery of the region of conductive fluid infusion is greater, since resistance is higher. Thus, the thermal effect of generally at the distal end of catheter 320; and a second, designated with reference numeral 324 spaced proximally back from the distal end of catheter 320.

Figure 40:
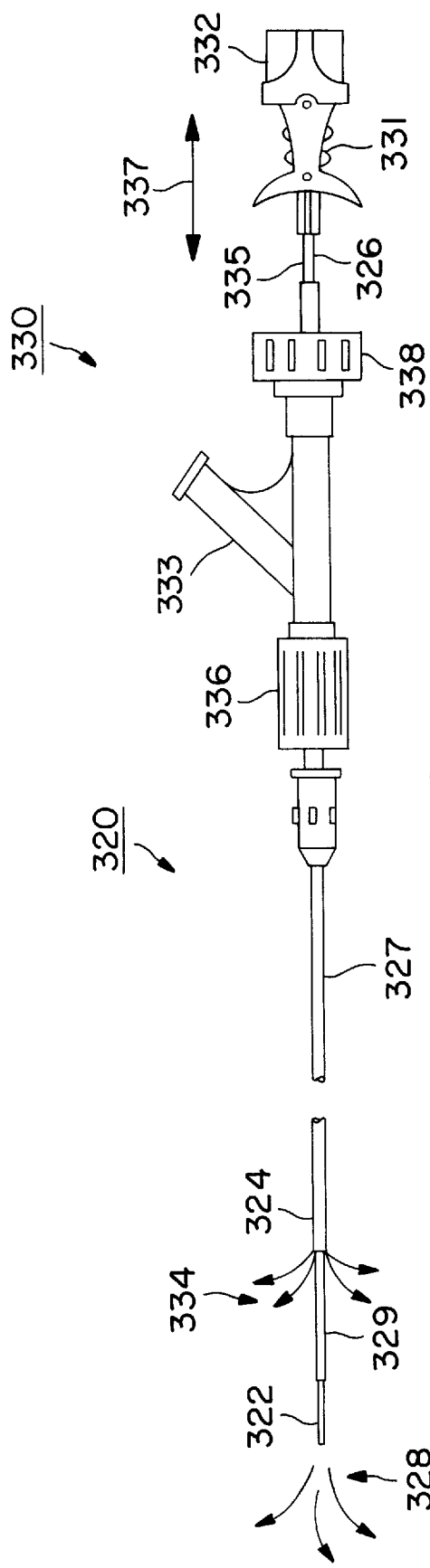
FIG. 40 is an enlarged cross-sectional view of the distal end of the bipolar ablation/hyperthermia catheter from FIG. 39.

Catheter 320 from FIG. 39 is shown in greater detail in FIG. 40. In one implementation of the embodiment of FIGS. 39 and 40, distal electrode 322 is defined by a non-insulated distal end of a flexible hypotube 326 which extends along the length of catheter 320, as in the embodiments previously described with reference to FIGS. 9–14, for example. Proximal electrode 324 is defined by a non-insulated portion of a second hypotube 327 which is coaxial with the first hypotube/electrode 326. A layer of insulation 329 electrically isolates hypotube 326 from hypotube 327.

Catheter 320 is provided at its proximal end with a manifold 330 similar to manifold 48 from the embodiment of FIG. 9, with two fluid couplings. One fluid coupling, designated with reference numeral 331, is used to supply infusion fluid (e.g., saline, saturated saline, or the like) to hypotube 326, such that fluid is expelled from the distal end thereof as indicated by arrows 328 in FIGS. 39 and 40. (A blocking stylet 332 may be inserted into hypotube 326 via fluid coupling 331 during introduction of catheter 320 to prevent hypotube 326 from being clogged during introduction. Stylet 332 is then removed to facilitate introduction of conductive fluid through hypotube 326. A second fluid coupling 333 is provided to facilitate injection of conductive fluid through outer hypotube 327, to be expelled as indicated by arrows 334.

Electrical coupling (for example, to the positive terminal of an RF generator, not shown) to inner hypotube/electrode 326 is made at the point designated 335 in FIG. 40, while electrical coupling (for example, to a negative terminal of an RF generator) to outer hypotube/electrode 327 is made through Luer lock 336. By coupling hypotube/electrodes 326 and 327 to opposite polarity terminals of the RF generator and delivering conductive fluid out of the ends thereof, an essentially ellipsoidal virtual electrode is established at the distal end of catheter 320, with electrodes 322 and 324 at the foci of the ellipse.

In one embodiment of the invention, inner hypotube 326 is slidable with respect to outer hypotube 327, as indicated by arrow 337. This advantageously allows the physician to adjust and control the distance between proximal and distal electrodes 324 and 322, thereby controlling the size and shape of the substantially ellipsoidal virtual electrode established as a result of conductive fluid injection in accordance with the present invention. Once the appropriate distance is achieved, a sealing ring can be tightened to prevent further sliding of hypotube 326 with respect to hypotube 327.

It is believed that the bipolar configuration of catheter 320 may allow for increased physician control over the size and shape of the virtual ablation electrode, since surrounding tissue and fluid is not relied upon to serve as the second electrode.

Figure 41:
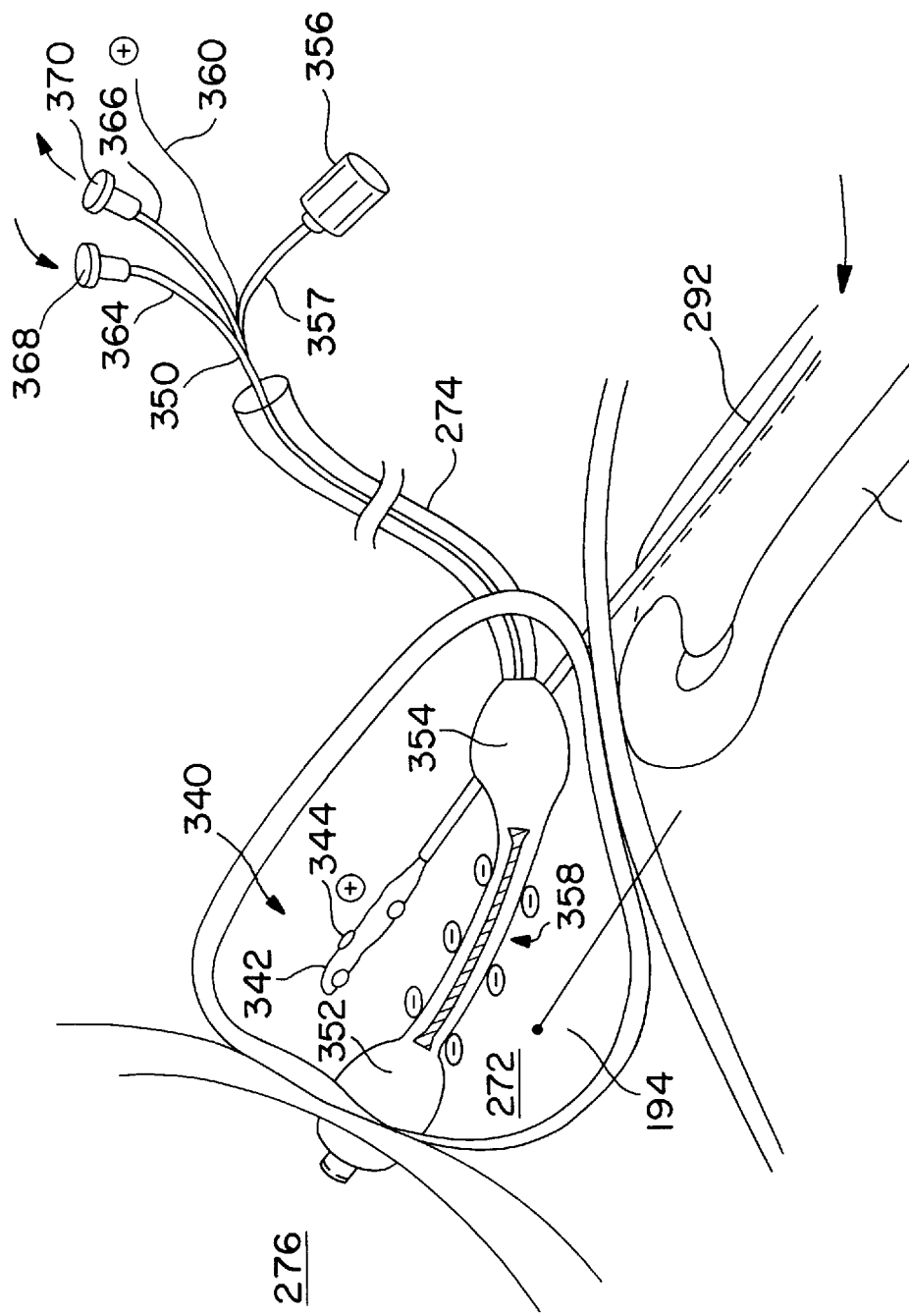
FIG. 41 is an illustration of a bipolar ablation/hyperthermia catheter system, including fluid-assisted catheter and a urethra cooling catheter, in accordance with another embodiment of the invention, being used for prostate ablation or hyperthermia.

Turning now to FIG. 41, there is illustrated an alternative arrangement for performing bipolar fluid-assisted in accordance with the present invention. In the arrangement of FIG. 41, a unipolar fluid-assisted ablation/hyperthermia catheter 340 is inserted into prostate 272 in accordance with the techniques described above with reference to FIGS. 28–31. Catheter 340 may have the configuration of any one of the different types of unipolar fluid-assisted catheters in accordance with the present invention, numerous embodiments of which having been described herein in detail. For example, catheter 340 may be of either the straight or screw-in types described herein. Distal electrode 342 of catheter 340 is coupled to a positive terminal of an RF generator (not shown), and is provided with fluid ports 344 to allow for fluid to be expelled therefrom to act as a virtual electrode in accordance with the present invention.

Figure 42:
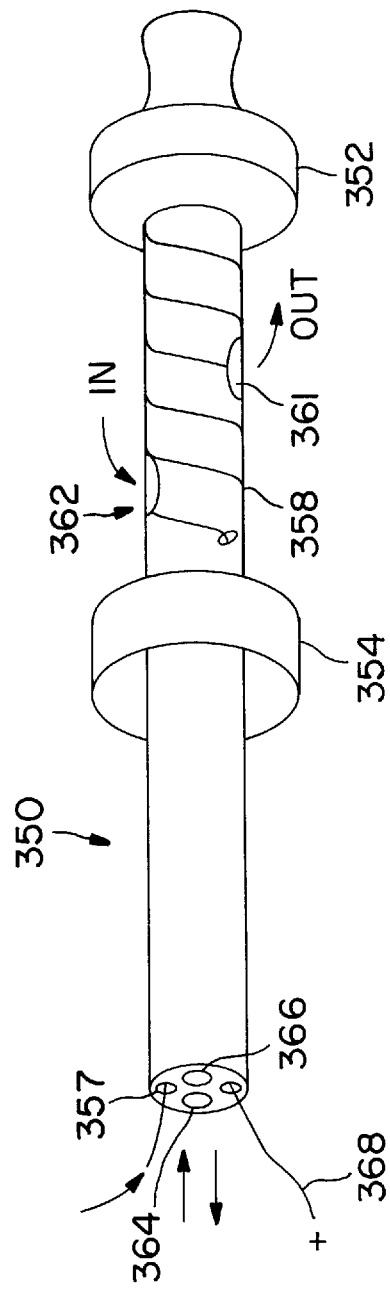
FIG. 42 is an enlarged view of the distal end of the urethral cooling catheter from FIG. 41.

In addition to catheter 340, the arrangement of FIG. 41 involves the use of a balloon-type urethral cooling catheter 350, the distal end of which is shown in greater detail in FIG. 42. Urethral cooling catheter 350 is provided with two balloons 352 and 354, one (352) at the distal end of catheter 350, and one (354) spaced proximally back from the distal tip of catheter 350. After introduction of catheter 350 into the urethra as depicted in FIG. 41, balloons 352 and 354 are inflated through injection of fluid into a fluid coupling 356 at the proximal end of catheter 350 and along an inflation lumen 357. When inflated, balloons 352 and 354 seal off a section of urethra 274, as shown in FIG. 41.

To establish a virtual electrode in accordance with the present invention, catheter 350 is also provided with an electrical connection 360 to be coupled to one terminal of an RF generator. A conductor 368 extends along the catheter body, and is coiled around an electrode section 358 of catheter 350 located between balloons 352 and 354.

Electrode section 358 is further provided with two fluid apertures 361 and 362 to allow for the inflow and outflow of conductive fluid communicated along catheter 350 via inflow and outflow lumens 364 and 366, respectively. Conductive fluid is delivered via a fluid coupling 368 and communicated along lumen 364 to be expelled from outflow aperture 361. The conductive fluid returns via inflow aperture 362, return lumen 366 and fluid coupling 370. Balloons 352 and 354 seal against the urethral wall, thereby containing the conductive fluid in electrode region 358 of catheter 350, establishing a virtual electrode in accordance with the present invention. It has been found that with the bipolar configuration depicted in FIG. 41 (i.e., with a virtual electrode of one polarity established by catheter 350 in the urethra, and a virtual electrode of the opposite polarity established by electrode 340 in the prostate 272), hyperthermic or ablative heating of prostate 272 can be accomplished while urethral temperatures are advantageously kept low enough to prevent damage to the urethra.

From the foregoing detailed description of various embodiments of the present invention, it should be apparent that methods and apparatuses for performing fluid-assisted ablation of various organs and tissues have been disclosed. Although From the foregoing detailed description of various embodiments of the present invention, it should be apparent that methods and apparatuses for performing fluid-assisted ablation of various organs and tissues have been disclosed. Although certain embodiments of the invention have been described herein in some detail, it is to be understood that this has been done merely to illustrate the present invention in various of its aspects, and is not intended to be limiting with respect to the scope of the invention as defined in the claims below. It is contemplated that a many substitutions, alterations, and/or modifications, including but not limited to those variations described herein, may be made to the embodiments disclosed without departing from the spirit and scope of the invention as defined in the following claims.

What is claimed is:

1. A prostate ablation catheter system, comprising:

an elongate catheter body having proximal and distal ends, a longitudinal fluid-conducting lumen extending between the proximal and distal ends, and an electrical conductor extending between the proximal and distal ends;

a hollow electrode in fluid communication with the longitudinal lumen at the distal end of the catheter body and in electrical contact with the electrical conductor at the distal end of the catheter body, the hollow electrode adapted to be introduced into a patient's prostate, and having at least one fluid port, the hollow electrode comprising:

an elongate needle having a distal portion with at least one distal fluid port for enabling fluid to be expelled therefrom, and a proximal portion in fluid communication with the catheter body lumen, the proximal portion having at least one proximal fluid port for enabling fluid to be expelled therefrom, and a balloon disposed circumferentially around the needle over the at least one proximal fluid port, such that fluid delivered to the needle via the catheter body lumen and expelled from the proximal fluid port inflates the balloon, the balloon thereby minimizing proximally-directed escape of fluid expelled from the distal fluid port;

a radio-frequency electrical generator coupled to the electrical conductor at the proximal end of the catheter body;

a source of conductive fluid, in fluid communication with the lumen at the proximal end of the catheter body, for delivering the conductive fluid through the lumen to be expelled from the fluid port into the prostate simultaneously with the application of energy from the generator to the prostate via the conductor and the electrode.

2. A prostate ablation catheter system in accordance with claim 1, in which the hollow electrode comprises a helical needle.

3. A prostate ablation catheter system in accordance with claim 1, further comprising a heat exchanger in fluid communication with the source of conductive fluid for cooling the fluid prior to delivery of the fluid through the catheter body lumen.

4. A prostate ablation catheter system in accordance with claim 1, further comprising a thermocouple, adapted to be inserted into the prostate at the periphery of the prostate area to be ablated, the thermocouple providing feedback to the generator to modulate the application of energy such that ablation temperature in the prostate is kept within predetermined limits.

5. A prostate ablation catheter system, comprising:
- a first elongate catheter having proximal and distal ends, a longitudinal fluid-conducting lumen extending between the proximal and distal ends, and an electrical conductor extending between the proximal and distal ends;
- a hollow electrode, having at least one conductive fluid port, which is in fluid communication with the longitudinal lumen at the distal end of the catheter body and in electrical contact with the electrical conductor at the distal end of the catheter body, the hollow electrode adapted to be introduced into a patient's prostate;
- a radio-frequency electrical generator coupled to the electrical conductor at the proximal end of the first catheter,
- a source of conductive fluid, in fluid communication with the lumen at the proximal end of the first catheter, for delivering the conductive fluid through the lumen to be expelled from the fluid port into the prostate simultaneously, with the application of energy from the generator to the prostate via the conductor and the electrode; and
- a urethral cooling catheter sub-system, comprising:
    - a second elongate catheter having proximal and distal ends and a longitudinal lumen extending between the proximal and distal ends, the second catheter being adapted to be introduced into a patient's urethra such that the distal end of the second elongate catheter is disposed in the urethra in the region of the prostate;
    - a third elongate catheter having an outer diameter which allows it to be introduced into the longitudinal lumen of the second catheter, the third catheter having proximal and distal portions and a longitudinal lumen extending between the proximal and distal portions, and further having at least one distal chilled fluid port disposed in the distal portion;
    - a source of cooled fluid, in fluid communication with the proximal portion of the third catheter, for delivering chilled fluid through the longitudinal lumen of the third catheter to be expelled from the at least one distal chilled fluid port;

such that when the second catheter is introduced into the urethra and the third catheter is introduced into the lumen of the second catheter, chilled fluid directed through the lumen of the third catheter is expelled from the distal chilled fluid port and communicated in the lumen of the second catheter to drain at the proximal end of the second elongate catheter, the flow of fluid through the second and third catheter lumens thereby cooling the urethra during ablation.

6. A prostate ablation catheter system in accordance with claim 5, in which the hollow electrode comprises a helical needle.

7. A prostate ablation catheter system in accordance with claim 5, in which the hollow electrode has a threaded conical configuration adapted to create pressure against prostate tissue into which it is screwed, thereby minimizing proximally-directed fluid escape.

8. A prostate ablation catheter system in accordance with claim 5, in which the hollow electrode comprises an expanding helical needle adapted to compress tissue into which it is screwed, thereby minimizing proximally-directed fluid escape.

9. A prostate ablation catheter system in accordance with claim 5, further comprising a heat exchanger in fluid communication with the source of conductive fluid for cooling the fluid prior to the delivery of the fluid through the catheter body lumen.

10. A prostate ablation catheter system in accordance with claim 5, further comprising a thermocouple, adapted to be inserted into the prostate at the periphery of the prostate area to be ablated, to provide feedback to the generator to modulate the application of energy such that ablation temperature in the prostate is kept within predetermined limits.

* * * * *